(12) United States Patent
Norris et al.

(10) Patent No.: US 9,914,917 B1
(45) Date of Patent: Mar. 13, 2018

(54) KEXIN-BASED VACCINES TO PREVENT OR TREAT FUNGAL INFECTIONS

(71) Applicants: Karen A. Norris, Pittsburgh, PA (US); Heather M. Kling, Pittsburgh, PA (US)

(72) Inventors: Karen A. Norris, Pittsburgh, PA (US); Heather M. Kling, Pittsburgh, PA (US)

(*) Notice: Subject to any disclaimer, the term of this patent is extended or adjusted under 35 U.S.C. 154(b) by 0 days.

(21) Appl. No.: 14/875,421

(22) Filed: Oct. 5, 2015

Related U.S. Application Data

(63) Continuation of application No. 14/088,250, filed on Nov. 22, 2013, now Pat. No. 9,181,538, which is a continuation-in-part of application No. 13/959,691, filed on Aug. 5, 2013, now Pat. No. 9,580,704, which is a continuation of application No. 13/521,621, filed as application No. PCT/US2011/020170 on Jan. 5, 2011, now abandoned.

(60) Provisional application No. 61/294,252, filed on Jan. 12, 2012.

(51) Int. Cl.
*C12N 9/58* (2006.01)
*A61K 38/19* (2006.01)
*A61K 39/00* (2006.01)

(52) U.S. Cl.
CPC ............ *C12N 9/58* (2013.01); *A61K 39/0002* (2013.01); *A61K 2039/53* (2013.01); *A61K 2039/541* (2013.01); *A61K 2039/543* (2013.01); *C12Y 304/21061* (2013.01)

(58) Field of Classification Search
None
See application file for complete search history.

(56) References Cited

U.S. PATENT DOCUMENTS

| 5,429,942 A | 7/1995 | Kock et al. |
| 5,442,050 A | 8/1995 | Fishman |
| 2008/0171053 A1 | 7/2008 | Gigliotti et al. |
| 2009/0326202 A1 | 12/2009 | Jackson et al. |

FOREIGN PATENT DOCUMENTS

| WO | WO 9839424 A1 * | 9/1998 | ............... C12N 9/58 |
| WO | WO 2011087934 A2 * | 7/2011 | ............... C12N 9/58 |

OTHER PUBLICATIONS

Ahlers, et al, "A push-pull approach to maximize vaccine efficacy: Abrogating suppression with an IL-13 inhibitor while augmenting help with granulocyte/macrophage colony-stimulating factor and CD4OL", *PNAS*, 99(20):13020-13025 (2002).
Beck, et al., "Inflammatory Responses to *Pneumocystis carinii* in Mice Selectively Depleted of Helper T Lymphocytes", *Am. I Respir. Cell Mot Biol.*, 5:186-197 (1991).

Harmsen, et al., "Requirement for CD4+ Cells in Resistance to *Pneumocystis carinii* Pneumonia in Mice", *J. Exp. Med.*, 17(2):937-945 (1990).
Kling, et al,, "Pneumocystis colonization in immunocompetent and simian immunodeficiency virus-infected cynomolgus macaques", J. Infect. Dis., 19(9):89-96 (2009 ).
Kling, et al., "Relationship of *Pneumocystis jiroveci* Humoral Immunity to Prevention of Colonization and Chronic Obstructive Pulmonary Disease in a Primate Model of HIV Infection", *Infection and Immunity*, 78(1):4320-4330 (2010).
Research in Progress for Humoral Response to Pneumocyistis Protects Immunosuppressed Macaques from Colonization and Subsequent Pulmonary function Decline, by Heather M. Kling, an oral presentation to MVM (Microbiology and Molecular Virology) Biochemistry and. Molecular Genetics Graduate program, 37 slides report from Nov. 2, 2009.
Kling et al., "Pneumocystis-Specific Antibodies Protect SHIV-Immunosuppressed Macaques from Colonization", *Biomedical Graduate Student Association*, Abstract presented as a poster in 2009.
Kling, et al., "*Pneumocystis*-Specific Antibodies Protect SHIV-Immunosuppressed Macaques from Colonization", *MVM-(Microbiology and Molecular Virology)*, Abstract and Platform talk 2009.
Kling, et al., "*Pneumocystis*-Specific Antibodies Protect SHIV-immunosuppressed Macaques from Colonization", *10th International Workshop of Protozoology*, Abstract and 26 slides presented as a platform talk at the meeting in May 2008.
Kokuchi, et al., "Dendritic Cells Genetically Modified to Express CD40 Ligand and Pulsed with Antigen can Initiate Antigen-Specific Hurnoral Immunity Independent of CD4+ T Cells", *Nature Medicine*, 6(10):1154-1159 (2000).
Kolls, et al., "Cytokine-Mediated Regulation of Antimicrobial Proteins", *Nature Reviews, Immunology*, 8(11):829-835 (2008).
Kolls, et al., "Gene Therapy to Modify Pulmonary Host Defenses", *Seminars in Respiratory Infections*, 16(1):18-26 (2001).
Arthur S. Levine, MD, Inquiry Panel Report on Allegations of Scientific Misconduct on the Part of Jay K. Kolls, MD (the "Report"), letter of Jul. 11, 2013, University of Pittsburgh.
"Inquiry Report on the Allegations of Research Misconduct on the Part of Drs. Jay K. Kolls and Mingquan Zheng", *University of Pittsburgh*, 20 pages (Jun. 21, 2013).
Kolls, et al., "IFN-y and CD8+ T Cells Restore Host Defenses Against *Pneumocystis carinii* in Mice Depleted of CDC T Cells", *The Journal of Immunology*, 16(2):2890-2894 (1999).
Karen A. Norris, Ph.D., "Letter to Provost Beeson, inquiry of misconduct by Dr. Jay Kolls", Letter to Dr. Patricia E. Beeson dated Apr. 8, 2013 (1 page).
Karen A. Norris, PhD., "Letter to Dr. Jerome Rosenberg, inquiry into possible research misconduct by Dr. Jay Kolls", *University of Pittsburgh*, letter to Dr. Jerome Rosenberg dated Sep. 20, 2011 (4 pages).

(Continued)

*Primary Examiner* — Brian Gangle
*Assistant Examiner* — Andrea K McCollum
(74) *Attorney, Agent, or Firm* — Melissa Hunter-Ensor; Leslie Serunian; Greenberg Traurig, LLP

(57) ABSTRACT

A vaccine is disclosed that promotes CD4+ T cell-independent host defense mechanisms to defend against infection by fungi such as *Pneumocystis* subspecies (spp.). The vaccine may be used to prevent or to treat fungal infections. The novel vaccine can provide protective immunity, even for immunocompromised individuals such as HIV patients having reduced levels of CD4+ T cells.

12 Claims, 5 Drawing Sheets

(56) References Cited

OTHER PUBLICATIONS

Karen A. Norris, Ph.D., "Letter to Lisa Borghesi Co-Chair from the School of Medicine and Rose Constantino Co-Chair from the School of Nursing, Tenure and Academic Freedom Committee (TAFC) in reference to procedural. issues", *University of Pittsburgh*, letter to Lisa Borghesi and Rose Constantino dated Nov. 13, 2012 (2 pages).
Dr. Jerome Rosenberg, "Letter to Karen A. Norris, PhD in reference to research misconduct of Jay Kolls", *University of Pittsburgh*, letter to Karen A. Norris dated Nov. 17, 2011.
Tenure and Academic Freedom Committee (TAFC), "Letter to Karen A. Norris in response to procedural issues", *University of Pittsburgh*, letter to Karen A. Norris dated Mar. 4, 2013.
Research in Progress, by Matt Gingo, in the Division of Pulmonary Allergy and Critical Care Medicine at the University of Pittsburgh, 37 slides report from Nov. 30, 2009.
McAllister, et al., "CXCR3 and IFN Protein-10 *Pneumocystis* pneumonia ", *The Journal of Immunology*, 17:1846-1854 (2006 ).
McAllister, et al., "In vitro Effector Activity of *Pneumocystis murina*-Specific T Cytotoxic-1 CDC T-Cells: Role of Granulocyte-Macrophage Colony-Stimulating Factor", *Infection and Immunity*, 73(11):7450-7457 (2005).
McAllister, et al., "T Cytotoxic-1 CDS* T Cells are Effector Cells against *Pneumocystis* in mice", *The Journal of Immunology*, 17(2):1132-1138 (2004).
McKinley, et al., Regulatory T Cells Dampen Pulmonary Inflammation and Lung Injury in an Animal Model of *Pneumocystis* Pneumonia , *The Journal of Immunology*, 177(9):6215-6226 (2006).
Ribas, at al., "CD 40 Cross-Linking Bypasses the Absolute Requirement for CDR T Cells During Immunization with Melanoma Antigen Gene-Modified Dendritic Cells", *Cancer Research*, 61:8787-8793 (2001).
Roths, et al., "Both Immunity and Hyperresponsiveness to *Pneumocystis carinii* Result from Transfer of CDC but not CDC T Cells into Severe Combined Immunodeficiency Mice", *The Journal of Clinical Investigation*, 90:673-678 (1992).
Shellito, et al., "A New Model of *Pneumocystis carinii* Infection in Mice Selectively Depleted of Helper T Lymphocytes", *The Journal of Clinical Investigation*, 85:1686-1693 (1990).
Simonds, et al., "Preventing *Pneumocystis carinii* Pneumonia in Persons Infected with Human Immunodeficiency Virus", *Clinigizl Infectious Diseases*, 21(Supp.11):S44-848 (1995).
Steele, et al., "Immunity Against the Opportunistic Fungal Pathogen *Pneumocystis*", *Medical Mycology*, 43:1-19 (2005).
Stone, et al., "Ivlultimpric Soluble CD40 Ligand and GITR Ligand as Adjuvants for Human Immunodeficiency Virus DNA Vaccines", *Journal of Virology*, 80(4):1762-1772 (2006 ).
Theus, et al., "Cytokine responses to the native and recombinant forms of the major surface glycoprotein of *Pneumocystis carinii*", *Clinical & Experimental Immunology*, 109:255-260 (1997).
Theus, et at, "Proliferative and Cytokine Responses to a Major Surface Glycoprotein of *Pneumocystis carinil*", *Infection and Immunity*, 61(11):4703-4709 (1993).
Wells, et al., "Complement and Fc Functin are Required for Optimal Antibody Prophylaxis against *Pneumocystis carinii* Pneumonia", *Infection and Immunity*, 74(1):390-393 (2006).
Zheng, et al., CDC T Cell-Independent Vaccination Against *Pneumocystis carinii* in Mice; *The Journal of Clinical Investigation*, 108:1469-1474 (2001).
Pittsburgh Post-Gazette, "A Timeline of Events in the Investigation of Pitt Scientist Jay Kolls", http://wwvv.post-gazette.com/stories/news/educationia-timeline-of-events-in-the-investigation-of-pitt-scientist-jay-kolls-689161/ dated May 26, 2013.
Pittsburgh Post-Gazette by Mark Roth, "University of Pittsburgh Clears Top Researcher of alleged Misconduct", http://www.post-gazette.com/stories/news/education/university-of-pittsburgh-clears-top-researcher-of-alleged-misconduct-695134/ dated Jul. 11, 2013.
Pittsburgh Post-Gazette by Mark Roth, "Pitt Researcher Kolls Reverses Stance on Vaccine Patent", http://www.post-gazette.com/stories/news/science/pitt-researcher-reverses-stance-on-vaccine-patent-690384/ dated Jun. 5, 2013.
Pittsburgh Post-Gazette by Mark Roth, "Expert: Pitt Researcher Jay Koll's Bid for Patent Could be at Risk", http://wwwpost-gazette.com/stories/news/healtb/expert-researchers-bid-for-patent-could-be-at-risk-689839/ dated May 31, 2013.
Pittsburgh Post-Gazette by Mark Roth, "Pitt Scientist Jay Kolls Faces Another Investigation", http://www.post-gazette.corn/stories/news/education/piU-scientist-jay-kolls-faces-another-investigation-689174/ dated May 26, 2013.
Zheng, et al., "CD4[+] T Cell-Independent DNA Vaccination Against Opportunistic Infections", *The Journal of Clinical Investigation*, 115:3536-3544 (2005).
Kling, et al., "Evaluation of Immunogenicity of a *Pneumocystis* Recombinant Protein Vaccine Candidate, Kexin; In Non-Human Primates" *Am J Respir Crit Care Med* 187;2013:A5569.
Wells, et al., "Active Immunization Against *Pneumocystis carinii* With a Recombinant *P. carinii* Antigen", *Infection and Immunity*, 74:2446-2448 (2006).
Lebedeva, et al., "Humoral Responses to *Pneumocystis* in a Simian Model of AIDS", *International Workshops on Opportunistic Protists*, 14 slides presented at the meeting in 2003.
Kling, H, "Humoral Immunity to the Opportunistic Pathogen, Pneumocystis, in a Simian Model of HIV Infection", PhD Dissertation, University of Pittsburgh, 2010.
Genbank Accession No. EU918304 "*Pneumocystis carinii* f. sp. *macacae* kexin mRNA, partial cds", Dec. 29, 2008.
In the United States District Court for the Western District of Pennsylvania, RE: *Karen A. Norris* vs. *University of Pittsburgh*; Case No. 2:14-CV-00120-CB; Dated Jan. 29, 2014. "Plaintiffs' Complaint Jury Trial Demanded", *Karen A. Norris, Ph.D. and Heather Kling, Ph.D.* vs. *University of Pittsburgh*, LSU Health Sciences Center—New Orleans, Board of Supervisors of LSU and Agricultural and—Mechanical College LSU Health• Sciences Center—New Orleans, Kay K. Kolls, M.D. from Richard King Mellon Foundation Institute for Pediatric Research Children's Hospital of Pittsburgh of Upmc, Mingquan Zhcng, M.D. from Richard King Mellon Foundation Institute for Pediatric Research Children's Hospital of Pittsburgh of UPMC and Minivax Corporation.
In the United States District Court for the Western District of Pennsylvania, Civil Action No. 2:14-CV-00120-CB, "Plaintiffs' Praecipe to Issue Summons", filed Feb. 4, 2014.
In the United States District Court for the Western District of Pennsylvania, Civil Action No. 2:14-CV-00120-CB, "Summons Issued. As to Board of Supervisors of LSU and Agricultural and Mechanical College, Jay K. Kolls, LSU Health Sciences. Center, Minivax Corporation, University of Pittsburgh, Mingquan Zheng". Filed Feb. 4, 2014.
In the United States District Court for the Western District of Pennsylvania, Civil Action No. 2:14-CV-00120-CB, "Summons Issued and Return of Service Returned Executed by Heather Kling, Karen A. Norris, University of Pittsburgh.". Entered Feb. 24, 2014.
In the United States District Court for the Western District of Pennsylvania, Civil Action No. 2:14-CV-00120-CB, "Summons Issued and Return of Service Returned Executed by Heather Kling, Karen A. Norris, LSU Health Sciences Center". Entered Feb. 24, 2014.
In the United States District Court for the Western District of Pennsylvania, Civil Action No. 2:14-CV-00120-CB, "Summons Issued and Return of Service Returned Executed by Heather Kling, Karen A. Norris, Jay K. Kolls". Entered Feb. 24, 2014.
In the United States District Court• for the Western District of Pennsylvania, Civil Action No. 2:14-CV-00120-CB, "Summons Issued and Return of Service Returned Executed by Heather Kling, Karen A. Norris, Board of Supervisors of LSU and Agricultural and Mechanical College". Entered Feb. 24, 2014.
In the United States District Court for the Western District of Pennsylvania, Civil Action No. 2:14-CV-00120-CB, "Summons Issued and Return of Service Returned Executed by Heather Kling, Karen A. Norris, Mingquan Zheng M.D.". Entered Feb. 24, 2014.
In the United States District Court for the Western District of Pennsylvania, Civil Action No. 2:14-CV-00120-CB, "Summons

(56) References Cited

OTHER PUBLICATIONS

Issued and Return of Service Returned Executed by. Heather Kling, Karen A. Norris, Minivax Corporation". Entered Feb. 24, 2014.
In the United States District Court for the Western District of Pennsylvania, Civil Action No. 2:14-CV-00120-CB, "Appearance of Counsel by Paula J. McDermott on behalf of Minivax Corporation". Entered Mar. 3, 2014.
In the United States DiStrict Court for the Western District of Pennsylvania, Civil Action No. 2:14-CV-00120-CB, "Defendant Minivax, Inc's, Motion to Dismiss: Motion to Dismiss for Lack of Jurisdiction by Minivax Corporation". Entered Mar. 3, 2014.
In the United States District Court for the Western District of Pennsylvania, Civil Action No. 2:14-CV-00120-CB, "Defendant Minivax, Inc's, Memorandum of Law in Support Its Motion to Dismiss". Entered Mar. 3, 2014.
In the United States District Court for the Western District of Pennsylvania, Civil Action No. 2:14-CV-00120-CB, "Disclosure Statement Identifying None as Corporate Parent or Other Affiliate, by Minivax Corporation". Entered Mar. 3, 2014.
In the United States District Court for the Western District of Pennsylvania, Civil Action No. 2:14-CV-00120-CB, "Stipulation to Extend the Time to Respond to Complaint by LSU Health Sciences Center, Board of Supervisors of LSU and Agricultural and Mechanical College; Answer due 4/17/20147 from LSU Health Sciences. Center, Board of Supervisors of LSU and Agricultural and Mechanical College ". Entered Mar. 3, 2014 (Modified Mar. 4, 2014).
In the United States District Court for the Western District of Pennsylvania, Civil Action No. 2:14-CV-00120-CB, "Appearance of Counsel by Vicki Kuftic Horne on behalf of Jay K. Kolls and Mingquan Zheng". Entered Mar. 5, 2014.
In the United States District Court for the Western District of Pennsylvania, Civil Action No. 2:14-CV-00120-CB, "Defendant University of Pittsburgh's Consent Motion for Extension". Entered Mar. 5, 2014.
In the United States District Court for the Western District of Pennsylvania, Civil Action No. 2:14-CV-00120-CB, "Order Granted: Upon consideration of Defendant University of Pittsburgh's Consent Motion for Extension". Entered Mar. 5, 2014.
In the United States District Court for the Western District of Pennsylvania, Civil Action No. 2:14-CV-00120-CB, "Defendant Kolls and Zheng's Consent Motion for Extension". Entered Mar. 5, 2014.
In the United States District Court for the Western District of Pennsylvania, Civil Action No. 2:14-CV-00120-CB, "Order Granted: Upon consideration of Defendant Kolls and Zheng's Consent Motion for Extension". Entered Mar. 5, 2014.
In the United States District Court for the Western District of Pennsylvania, Civil Action No. 2:14-CV-00120-CB, "Motion for Admission Pro Hac Vice of Paula J. Mcdermott on behalf of Minivax Corporation". Entered Mar. 12, 2014.
In the United States District Court for the Western District of Pennsylvania, Civil Action No. 2:14-CV-00120-CB, "Affidavit of Paula J. Mcdermott in Support of Motion for Admission Pro Hag Vice on behalf of Minivax Corporation". Entered Mar. 12, 2014.
In the United States District Court for the Western District of Pennsylvania, Civil Action No. 2:14-CV-00120-CB, "Exhibit 1: Certificate of Good Standing of Paula J. McDermott". Entered Mar. 12, 2014.
In the United States District Court for the Western District of Pennsylvania, Civil Action No. 2:14-CV-00120-CB, "(Proposed) Order and Granted of Paula J. McDermott to Appear and practice in the Court". Entered Mar. 12, 2014.
In the United States District Court for the Western District of Pennsylvania, Civil Action No. 2:14-CV-00120-CB, "Defendant University of Pittsburgh's Motion to Dismiss, or, in the Alternative, for Summary of Judgment". Entered Mar. 14, 2014.
In the United States District Court for the Western District of Pennsylvania, Civil Action No. 2:14-CV-00120-CB, "Declaration of Marc S. Malandro Re: Defendant University of Pittsburgh's Motion to Dismiss, or, in the Alternative, for Summary of Judgment". Entered Mar. 14, 2014.
In the United States District Court for the Western District of Pennsylvania, Civil Action No. 2:14-CV-00120-CB, "Defendant University of Pittsburgh's Brief in Support of Motion to Dismiss, or, in the Alternative, for Summary of Judgment". Entered Mar. 14, 2014.
In the United States District Court for the Western District of Pennsylvania, Civil Action No. 2:14-CV-00120-CB, "Defendants Kolls and Zheng's Motion To Dismiss, or, in the Alternative, for Summary of Judgment". Entered Mar. 14, 2014.
In the United States District Court for the Western District of Pennsylvania, Civil Action No. 2:14-CV-00120-CB, "Defendants Kolls and Zheng's Brief in Support of Motion to Dismiss, or, in the Alternative, for Summary of Judgment". Entered Mar. 14, 2014.
In the United States District Court for the Western District of Pennsylvania, Civil Action No. 2:14-CV-00120-CB, "Defendant University of Pittsburgh'S Disclosure Statement". Entered Mar. 17, 2014.
In the United States District Court for the Western District of Pennsylvania, Civil Action No. 2:14-CV-00120-CB, "Appearance of Counsel by David J. Porter on behalf of University of Pittsburgh". Entered Mar. 17, 2014.
In the United States District Court for the Western District of Pennsylvania, Civil Action No. 2:14-CV-00120-CB, "Appearance of Counsel by Michael L. Denver on behalf of University of Pittsburgh". Entered Mar. 17, 2014.
In the United States District Court for the Western District of Pennsylvania, Civil Action No. 2:14-CV-00120-CB, "Appearance of Counsel by Alexandra P. West on behalf of University of Pittsburgh". Entered Mar. 17, 2014.
In the United States District Court for the Western District of Pennsylvania, Civil Action No. 2:14-CV-00120-CB, "Motion for Admission Pro Hac Vice of Jason L. Reimer on behalf of Minivax Corporation". Entered Mar. 19, 2014.
In the United States District Court for the Western District of Pennsylvania, Civil Action No. 2:14-CV-00120-CB, "Affidavit of Jason L. Reimer in Support of Motion for Admission Pro Hac Vice on behalf of Minivax Corporation". Entered Mar. 19, 2014.
In the United States District Court for the Western District of Pennsylvania, Civil Action No. 2:14-CV-00120-CB, "Exhibit 1: Certificate of Good Standing of Jason Lawrence Reimer, Esq.". Entered Mar. 19, 2014.
In the United States District Court for the Western District of Pennsylvania, Civil Action No. 2:14-CV-00120-CB, "(Proposed) Order and Granted of Jason L. Reimer to Appear and practice in the Court". Entered Mar. 19, 2014.
In the United States District Court for the Western District of Pennsylvania, Civil Action No. 2:14-CV-00120-CB, "Plaintiffs' Response to Defendant Minivax's Motion to Dismiss by Kling and Norris". Entered Mar. 24, 2014.
In the United States District Court for the Western District of Pennsylvania, Civil Action No. 2:14-CV-00120-CB, "Plaintiffs' Memorandum of Law in Support of Their Response to Defendant Minivax's Motion to Dismiss by Kling and Norris". Entered Mar. 24, 2014.
In the United States District Court for the Western District of Pennsylvania, Civil Action No. 2:14-CV-00120-CB, "Plaintiffs' Response to Defendant University of Pittsburgh's Motion to Dismiss or, in the Alternative, Summary Judgment by Kling and Norris". Entered Apr. 3, 2014.
In the United States District Court for the Western District of Pennsylvania, Civil Action No. 2:14-CV-00120-CB, "Plaintiffs' Response to Defendants Jay Kolls, M.D. and Mingquan Zheng, M.D.'s Motion to Dismiss or, in the Alternative, Summary Judgment by Kling and Norris". Entered Apr. 3, 2014.
In the United States District Court for the Western District of Pennsylvania, Civil Action No. 2:14-CV-00120-CB, "Plaintiffs' Memorandum of Law in Support of Their Response to Defendants Kolls and Zheng's Motion to Dismiss or, in the Alternative, Summary Judgment by Kling and Norris". Entered Apr. 4, 2014.

(56) References Cited

OTHER PUBLICATIONS

In the United States District Court for the Western District of Pennsylvania, Civil Action No. 2:14-CV-001207CB, "Plaintiffs' Memorandum of Law in Support of Their Response to Defendant University of Pittsburgh's Motion to Dismiss or, in the Alternative, Summary Judgment by Kling and Norris". Entered Apr. 3, 2014.
In the United States District Court for the Western District of Pennsylvania, Civil Action No. 2:14-CV-00120-CB, "Defendant University of Pittsburgh's Reply Brief in Support of Motion to Dismiss, or, in the Alternative, for Summary Judgment". Entered Apr. 10, 2014.
In the United States District Court for the Western District of Pennsylvania, Civil Action No. 2:14-CV-00120-CB, "Defendants Jay K. Kolls M.D. & Mingquan Zheng M.D.'s Reply Brief". Entered Apr. 10, 2014.
In the United States District Court for the Western District of Pennsylvania, Civil Action No. 2:14-CV-00120-CB, "Plaintiffs' Sur Reply to the University of Pittsburgh's Reply Brief in Support of Motion to Dismiss or in the Alternative, for Summary Judgment". Entered Apr. 10, 2014.
In the United States District Court for the Western District of Pennsylvania, Civil Action No. 2:14-CV-00120-CB, "Defendants Board of Supervisors of LSU and Agricultural and Mechanical College and LSU Health Sciences Center—New Orleans' Motion to Dismiss". Entered Apr. 17, 2014.
In the United States District Court for the Western District of Pennsylvania, Civil Action No. 2:14-CV-00120-CB, "Defendants Board. of Supervisors of LSU and Agricultural and Mechanical College and LSU Health Sciences Center—New Orleans' Brief in Support of Motion to Dismiss". Entered Apr. 17, 2014.
In the United States District Court for the Western District of Pennsylvania, Civil Action No. 2:14-CV-00120-CB, "Notice of Appearance of Christopher M. Verdian on behalf of Board of Supervisors of LSU and Agricultural and Mechanical College and LSU Health Sciences Center—New Orleans". Entered Apr. 17, 2014.
In the United States District Court for the Western District of Pennsylvania, Civil Action No. 2:14-CV-00120-CB, "Notice of Appearance of Anna Shabalov on behalf of Board of Supervisors of LSU and Agricultural and Mechanical College and LSU Health Sciences Center—New Orleans". Entered Apr. 17, 2014.
In the United States District Court for the Western District of Pennsylvania, Civil Action No. 2:14-CV-00120-CB, "Plaintiffs, Karen A. Norris, Ph.D., and Heather Kling, Ph.D.'s Response to Defendant, Board of Supervisors of LSU and Agricultural and Mechanical College and LSU Health Sciences Center—New Orleans' Motion to Dismiss". Entered May 7, 2014.
In the United States District Court for the Western District of Pennsylvania, Civil Action No. 2:14-CV-00120-CB, "Plaintiffs' Memorandum of Law in Support of Their Response to Defendant, Board of Supervisors of LSU and Agricultural and Mechanical College and LSU Health Sciences Center—New Orleans' Motion to Dismiss". Entered May 7, 2014.
In the United States District Court for the Western District of Pennsylvania, Civil Action No. 2:14-CV-00120-CB, "Defendants Board of Supervisors of LSU and Agricultural and Mechanical College's and LSU Health Sciences Center—New Orleans' Reply Brief on Support of Motion to Dismiss". Entered May 14, 2014.
In the United States District Court for the Western District of Pennsylvania, Civil Action No. 2:14-CV-00120-CB, "Plaintiffs' Motion to Supplement the Record As to the Pending Motions to Dismiss". Plaintiffs, Dr. Karen A. Norris and Dr. Heather Kling hereby move to supplement the record as to the Motions to Dismiss filed by Defendants University of Pittsburgh, Dr. Jay Kolls, and Dr. Mingquan Zheng, Entered Aug. 19, 2014.
In the United States District Court for the Western District of Pennsylvania, Civil Action No. 2:14-CV-00120-CB, Plaintiffs' Motion to Supplement Record as to Pending MTD Proposed Order, "Order Granted: Upon consideration of Plaintiffs' motion to supplement the record with regard to the motions to dismiss filed by Defendant University of Pittsburgh and Defendants Dr. Kolls and Dr. Zheng". Entered Aug. 19, 2014.
In the United States District Court for the Western District of Pennsylvania, Civil Action No. 2:14-CV-00120-CB, Plaintiff Motion to Supplement Record Ex. Demanded Assignment, "Memorandum From University of Pittsburgh: Re: Required Intellectual Property Rights Assignment for Faculty and Non-Clerical Staff, dated Aug. 4, 2014". Entered Aug. 19, 2014.
In the United States District Court for the Western District of Pennsylvania, Civil Action No. 2:14-CV-00120-CB, "Plaintiff Motion to Supplement Record Ex. Patent Office Action". Entered Aug. 19, 2014.
In the United States District Court for the Western District of Pennsylvania, Civil Action No. 2:14-CV-00120-CB, Plaintiff Motion to Supplement Record Ex. UPitt Counsel Letter; "Re: *Karen Norris et al* v. *University of Pittsburgh et al* No. 14-120-CB, letter dated Aug. 6, 2014". Entered Aug. 19, 2014.
In the United States District Court for the Western District of Pennsylvania, Civil Action No. 2:14-CV-00120-CB, Plaintiff Motion to Supplement Record Ex. Plaintiffs' Counsel Letter; "Re: Joint Research and Material Transfer Agreement, letter dated Aug. 5, 2014". Entered Aug. 19, 2014.
In the United States District Court for the Western District of Pennsylvania, Civil Action No. 2:14-CV-00120-CB, Plaintiff Motion to Supplement Record Ex. Rejected Assignment; "Re: Intellectual Property Rights Assignment, signed by Karen A. Norris on Aug. 8, 2014". Entered Aug. 19; 2014.
In the United States District Court for the Western District of Pennsylvania, Civil Action No. 2:14-CV-00120-CB, "Plaintiffs' Memorandum of Law in Support of Their Motion to Supplement the Record". Entered Aug. 19, 2014.
In the United States District Court for the Western District of Pennsylvania, Civil Action No. 2:14-CV-00120-CB, "Defendant University of Pittsburgh's Opposition to Plaintiffs' Motion to Supplement the Record As to the Pending Motions to Dismiss, With Supporting Authorities". Entered Aug. 26, 2014.
In the United States District Court for the Western District of Pennsylvania, Civil Action No. 2:14-CV-00120-CB, "Defendant Jay K. Kolls M.D. & Mingquan Zheng M.D.'s Response in Opposition to Plaintiffs' Motion to Supplement the Record and to Strike Impertinent or Scandalous Matter", Entered Aug. 26, 2014.
In the United States District Court for the Western District of Pennsylvania, Civil Action No. 2:14-CV-00120-CB, "Supplement to Defendant University of Pittsburgh's Brief-In Support of Motion to Dismiss, or, in the Alternative, for Summary Judgment Defendant", Entered Aug. 28, 2014.
In the United States District Court for the Western District of Pennsylvania, Civil Action No. 2:14-CV-00120-CB, "Supplement to Defendant University of Pittsburgh'S Brief in Support of Motion to Dismiss, or, in the Alternative, for Summary Judgment Defendant, Exhibit A", Entered Aug. 28, 2014.
In the United States District Court for the Western District of Pennsylvania, Civil Action No. 2:14-CV-00120-CB, "Plaintiffs' Rule 56(d) Affidavit Support of Additional Discovery", Entered Sep. 15, 2014.
In the United States District Court for the Western District of Pennsylvania, Civil Action No. 2:14-CV-00120-CB, "Plaintiffs' Rule 56(d) Affidavit Support of Additional Discovery, Exhibit A", Entered Sep. 15, 2014.
In the United States District Court for the Western District of Pennsylvania, Civil Action No. 2:14-CV-00120-CB, "Plaintiffs' Rule 56(d) Affidavit Support of Additional Discovery, Exhibit B", Entered Sep. 15, 2014.
In the United States District Court for the Western District of Pennsylvania, Civil Action No. 2:14-CV-00120-CB, "University of Pittsburgh's Motion to Strike Plaintiffs' Rule 56(d) Affidavit in Support of Additional Discovery", Entered Sep. 16, 2014.
In the United States District Court for the Western District of Pennsylvania, Civil Action No. 2:14-CV-00120-CB, "University of Pittsburgh'S Motion to Strike Plaintiffs' Rule 56(d) Affidavit in Support of Additional Discovery Proposed Order", Entered Sep. 16, 2014.

(56) References Cited

OTHER PUBLICATIONS

In the United States District Court for the Western District of Pennsylvania, Civil Action No. 2:14-CV-00120-CB, "Plaintiffs' Response to Defendants' Response to Defendants' Motion to Strike Plaintiffs' Rule 56(d) Affidavit", Entered Sep. 22, 2014.

In the United States District Court for the Western District of Pennsylvania, Civil Action No. 2:14-CV-00120-CB, "Plaintiffs' Response to Defendants' Motion to Strike Plaintiffs' Rule 56(d) Affidavit Proposed Order", Entered Sep. 22, 2014.

In the United States District Court for the Western District of Pennsylvania, Civil Action No. 2:14-CV-00120-CB, "Defendant the University of Pittsburgh Order Granting Motion. To Dismiss", Entered Dec. 10, 2014.

In the United States District Court for the Western District of Pennsylvania, Civil Action No. 2:14-CV-00120-CB, "Judgment Order", Entered Dec. 10, 2014.

In the United States District Court for the Western District of Pennsylvania, Civil Action No. 2:14-CV-00120-CB, "Notification of Decision Sent to Commissioner of Patents and Trademarks", Entered Dec. 12, 2014.

\* cited by examiner

US 9,914,917 B1

SEQUENCE LISTING

```
<160> NUMBER OF SEQ ID NOS: 7

<210> SEQ ID NO 1
<211> LENGTH: 90
<212> TYPE: PRT
<213> ORGANISM: Pneumocystis jirovecii

<400> SEQUENCE: 1

Asp Asp Asp Gly Lys Thr Val Asp Gly Pro Ser Ser Leu Val Leu Arg
1               5                   10                  15

Ala Leu Ile Asn Gly Val Asn Asn Gly Arg Asn Gly Leu Gly Ser Ile
            20                  25                  30

Tyr Val Phe Ala Ser Gly Asn Gly Gly Ile Tyr Glu Asp Asn Cys Asn
        35                  40                  45

Phe Asp Gly Tyr Ala Asn Ser Val Phe Thr Ile Thr Ile Gly Gly Ile
    50                  55                  60

Asp Lys His Gly Lys Arg Leu Lys Tyr Ser Glu Ala Cys Ser Ser Gln
65                  70                  75                  80

Leu Ala Val Thr Tyr Ala Gly Gly Ser Ala
            85                  90

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgaggtgaa aagtcgaaag gg                                              22

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(4)
<223> OTHER INFORMATION: Inosine
<220> FEATURE:
```

```
<221> NAME/KEY: modified_base
<222> LOCATION: (25)..(25)
<223> OTHER INFORMATION: Inosine

<400> SEQUENCE: 3
tgantgtctc agatgaaaaa cctcnt                                           26

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (24)..(24)
<223> OTHER INFORMATION: Inosine
<220> FEATURE:
<221> NAME/KEY: modified_base
<222> LOCATION: (32)..(32)
<223> OTHER INFORMATION: Inosine

<400> SEQUENCE: 4
acagcccaga ataatgaata aagntcctca antgttac                              38

<210> SEQ ID NO 5
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 agtcagtc                                                               8

<210> SEQ ID NO 6
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 aatcaatc                                                               8

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 agtgtc                                                                 6
```

KEXIN-BASED VACCINES TO PREVENT OR TREAT FUNGAL INFECTIONS

CROSS-REFERENCE TO RELATED APPLICATIONS

This application is a continuation of U.S. patent application Ser. No. 14/088,250 filed on Nov. 22, 2013, now allowed, which is a continuation-in-part of U.S. patent application Ser. No. 13/959,691 filed Aug. 5, 2013, which is a continuation of U.S. patent application Ser. No. 13/521,621, filed Nov. 12, 2012, which is the U.S. National Stage pursuant to 35 U.S.C. § 371 of International Application No. PCT/US2011/020170, filed Jan. 5, 2011, which claims the benefit of and priority to U.S. provisional patent application Ser. No. 61/294,252, filed Jan. 12, 2010 under 35 U.S.C. § 119(e) in the United States, and is claimed under applicable treaties and conventions in all countries. The disclosures of each of the foregoing patent applications are incorporated herein in their entireties by reference.

The specification incorporates by reference the Sequence Listing submitted herewith via EFS on Jul. 21, 2017. Pursuant to 37 C.F.R. § 1.52(e)(5), the Sequence Listing text file, identified as 167746_010204_SL.txt, is 2,933 bytes and was created on Jun. 23, 2017. The Sequence Listing, electronically filed herewith, does not extend beyond the scope of the specification and thus does not contain new matter.

STATEMENT OF RIGHTS TO INVENTIONS MADE UNDER FEDERALLY SPONSORED RESEARCH

This invention was made with government support under grant HL077095; RO1 HL077914, and 1R56AI091576 awarded by the National Institutes of Health. The United States Government has certain rights in this invention.

TECHNICAL FIELD

This invention pertains to certain proteins derived from Kexin, nucleic acids encoding those proteins, and the use of the proteins or nucleic acids as vaccines, for example, as vaccines against *Pneumocystis jirovecii* or other *Pneumocystis* subspecies (spp.).

BACKGROUND ART

Epidemiology of *Pneumocystis* Infection

Despite advances in highly active anti-retroviral therapy (HAART), opportunistic pulmonary infection with *Pneumocystis* (PC) remains the most common opportunistic infection for HIV patients. Indeed, *Pneumocystis* pneumonia (PCP) is the index infection for 25-40 percent of AIDS cases. In patients with established AIDS, prophylactic regimens have decreased the overall incidence of PCP, but in most patients this means that PCP is delayed rather than eliminated. For example, in patients with CD4 counts below 200/h1 who are on recommended prophylactic regimens, there is still approximately an 18% risk of active PCP infection over a 36 month period. The widespread use of PCP prophylaxis also means that more than 80% of PCP cases in the U.S. are now "breakthrough" cases. Moreover, one study of high-risk children found that the incidence of PCP had not declined despite efforts to identify HIV-infected infants and to initiate PCP prophylaxis for them.

There is a strong correlation between a higher CD4+ T cell count and a lower risk of PCP. Where HAART is successful, as shown by an increase in a patient's CD4+ T-cell count above 2001 ul, available data suggest that PCP prophylaxis can be safely discontinued. Unfortunately, not all AIDS patients respond to HAART, and drug resistance is emerging. PCP is still a serious clinical problem in the third decade of the HIV epidemic. There is an unfilled need for improved methods for PCP prevention and treatment.

In AIDS the depletion or dysfunction of CD4+ lymphocytes not only hinders the patient's immune response to infection, it also reduces or eliminates the ability to safely and effectively vaccinate a patient against PCP. *Pneumocystis* is a genus of fungi that is found in the respiratory tracts of many mammals and humans *Pneumocystis* infection is easily defended by a healthy immune system. The symptoms of PCP infection include pneumonia, fever, and respiratory symptoms such as dry cough, chest pain and dyspnea. Currently, antibiotics are the preferred method of treatment, along with corticosteroids in some severe cases. The most popular antibiotic, and the accepted benchmark for efficacy is Trimethoprim-sulfamethoxazole (TMP-SMX). Alternative antibiotics are also available due to the severe allergic reactions that some people have to TMP-SMX. Studies have shown that individuals who are on highly active antiretroviral therapies (HAART), and who have CD4+ T-cell counts above a threshold of about 200 cells/mm$^3$ have a sufficient immune response to defend against PCP infection without antibiotics. Prophylaxis is recommended for HIV-positive individuals once their CD4+ T cell count falls below 200 cells/mm$^3$, and is also recommended for other severely immunocompromised patients such as transplant patients or leukemia patients. Drug prophylaxis reduces the incidence of PCP and lengthens the disease free intervals between episodes. However, the most effective prophylactic treatment, TMP-SMX, has a high rate of adverse effects. Second-line drugs may be used, but they typically have serious side effects and generally are less effective.

PCP infection will occur in approximately 15%-28% of individuals with AIDS in a given year. Within the population of HIV/A1DS patients with PCP, the mortality rate is between 10%-20%. An estimated 1 million people worldwide suffer from PCP, while another 5 million people are treated prophylactically to prevent the disease. Definitive diagnosis of *Pneumocystis* pneumonia is relatively complex, requiring microscopy of tissues or fluids. As PCP prophylaxis and HAART become more widespread, the incidence of PCP has declined in populations where infection can be properly diagnosed and treatment can be administered. Studies suggest that the low prevalence figures reported from developing countries may simply reflect the lack of adequate infrastructure to properly diagnose PCP.

Organ transplant recipients are also at risk for PCP infection. Transplant recipients take regimens of anti-rejection drugs that function by suppressing the immune system. The overall incidence of PCP in solid organ transplant recipients not taking PCP prophylaxis is about 5%, with the highest incidence following liver, heart, and lung transplants. The most common prophylaxis currently used for organ transplant patients is TMP-SMX, or aerosolized pentamidine if TMP-SMX is not tolerated by the patient.

Most currently available antibiotic treatments have mild to severe side effects, leaving an unfilled need for alternative treatments. Additionally, antibiotic-resistant *Pneumocystis* are emerging, in part because some patients cease treatment due to allergic reaction or other adverse effects.

Host Defense and *Pneumocystis* Infection

The inability to reliably culture *Pneumocystis* organisms in vitro has limited experimental work with the pathogen to clinical specimens and animal models of infection. Human *Pneumocystis* infection is associated more with defects in cell-mediated immunity than with neutrophil dysfunction. *Pneumocystis* infections are a particular clinical problem in AIDS patients, whose progressive loss of CD4+ helper T lymphocytes results in profound suppression of cell-mediated immunity. The risk of an mv-infected adult acquiring PCP shows an inverse, and almost linear correlation with the number of circulating CD4+ lymphocytes. A similar relationship has also been seen for in pediatric PCP infection, although the relative CD4+ count may be higher in children. The importance of CD4+ T lymphocytes in host defense against PCP is further supported by work with animal models. For example, experimental work from our laboratory shows that normal mice inoculated with *P. murina* are able to resolve the infection without treatment, while mice that have been specifically and selectively depleted of CD4+ T lymphocytes with an anti-CD4 monoclonal antibody develop progressive PCP. When administration of the antibody cease and CD4+ lymphocytes are restored, *P. murina* organisms are cleared from lung tissue and the PCP infection resolves.

CD4+ T-Cell Factors in *Pneumocystis* Infection

Among the mechanisms used by CD4+ lymphocytes to mediate host defense against *Pneumocystis* is the secretion of cytokines such as interferon (IFN). Lymphocytes exposed to PC organisms or to the major surface glycoprotein of PC in vitro will secrete IFN. However, lymphocytes from AIDS patients have a reduced capacity to produce IFN after antigenic or mitogenic stimulation. Although IFN is not directly lethal to *Pneumocystis*, ii can activate macrophages in vitro to kill the organism. However, evidence for an in vivo role for IFN in host defense is conflicting. In vivo neutralization of IFN with an antibody has been reported not to alter clearance of *P. murina* in reconstituted SCID mice. Also, SCID mice that had been reconstituted with splenocytes from mice with a homozygous deletion of the IFN gene were nevertheless able to reduce levels of *P. murina* infection.

It has been postulated that a potential target cell for exogenous IFN is the alveolar macrophage cell, because aerosolized IFN will augment expression of these cells. It has been demonstrated that depletion of alveolar macrophages leads to delayed clearance of *P. carinii* from the rat lung.

Possible mechanisms for IFN bolstering of host defense include up-regulation of TNF production, increased generation of superoxide, and increased release of reactive nitrogen intermediates.

Overexpression of interferon by gene delivery results in augmented clearance of *P. murina*, which depends in part on enhanced recruitment of CXCR3+ CD8+ T-cells. Although IFN is clearly therapeutic, endogenous IFN is not required; for example, IFN-gamma knockout (KO) mice can clear *P. murina* infection.

CD40L and T- and B-Cell Immune Responses and Host Defense Against PC

CD40L is another factor that is expressed on CD4+ T cells, and that is critical for host defense against PCP. CD40L (also known as CD154) is a 33 kDa, type II membrane protein. It is a member of the tumor necrosis factor (TNF) gene family, and it is a ligand for CD40 on antigen presenting cells (APC) such as dendritic cells (DCs) and B cells. It has been recently shown that CD40L expression in CD4+ T cells is critical for T cell "help," and permits direct interactions between APCs and CD8+ cytotoxic T cells. Moreover, as CD40 is also expressed on B cells, up-regulation of CD40L on CD4+ T cells also is a critical component of T helper function to induce B cell proliferation.

CD40L:CD40 interactions appear critical for effective host defense against PC. Patients with missense or nonsense mutations in CD40L often have hyper-IgM syndrome. Hyper-IgM syndrome results from a lack of B-cell differentiation. Patients with hyper-IgM syndrome are often infected with PC. Antibody blockage of CD40L:CD40 interactions prevents splenocyte-reconstituted scid mice from clearing PCP infection. Indeed, 4-6 week old CD40L knockout mice from a respected laboratory have been inadvertently shipped infected with PC. Soluble CD40L has been reported to have a beneficial effect against PCP in a steroid-induced immunosuppressed rat model.

DCs genetically engineered to express CD40L have been reported to present antigens (from *Pseudomonas aeruginosa*) to B-cells both in vitro and in vivo in a CD4-independent manner. The resulting antibodies conferred protection against in vivo challenge with the bacteria.

Our laboratory has previously reported the use of kexin, which is a PC antigen, in a DNA vaccine with or without CD40L. See M. Zheng et al., "CD4+ T cell-independent DNA vaccination against opportunistic infections," J Clin. Invest., vol. 115, pp. 3536-3544 (2005). Despite the promise of Kex 1 DNA vaccination, there remains an unfilled need for improvements to the earlier vaccine. Vaccination with the Kex 1 DNA resulted in only a 2-3 log improvement in protection as compared to controls; mice challenged after Kex1 vaccination still have detectable infection histologically at 28 days post-PC challenge.

Rationale for a *Pneumocystis* Vaccine

The pathogenesis of HIV infection involves profound immunosuppression, which leads to greatly increased susceptibility to infections. Most opportunistic infections in HIV patients involve the respiratory tract. Pneumonia caused by the fungal pathogen *Pneumocystis jirovecii* remains the most common AIDS-defining opportunistic infection. Antimicrobial therapies are available, but emerging antimicrobial resistance is making treatments less effective. Furthermore, high drug costs can preclude antimicrobial therapy in many third world countries have high rates of HIV infection. Even in developed countries, 20-30% of eligible patients do not receive prophylaxis, either because of noncompliance or because of the cost of the medications Also, *Pneumocystis* colonization is no longer confined to the HIV-infected population. *Pneumocystis* spp. are incredibly successful pathogens, being found in all areas of the world and in numerous animal species. PCP infection carries a high mortality rate. There remains a pressing, unfilled need for new vaccines and vaccination approaches to prevent or treat mV-associated pulmonary infections.

Molecular techniques have recently shown that *Pneumocystis* colonization of the respiratory tract is common in many non-HIV-associated pulmonary diseases, such as emphysema, where PCP can lead to a systemic inflammatory response and accelerated progression of obstructive airway disease. Thus, a vaccine against *Pneumocystis* can prevent not just the development of pneumonia, but may also limit co-morbidities of HIV infection, emphysema, and other diseases.

Potential candidates to receive a *Pneumocystis* vaccine would include individuals who are currently candidates for PCP prophylaxis, such as HIV-infected persons with a CD4 count below 200; and patients receiving immunosuppressive drugs including high-dose corticosteroids, and receiving anti-inflammatory agents such as anti-TNF and anti-B-lymphocyte agents. Such patients would include transplant recipients, cancer patients (including leukemia and lymphoma patients), and patients with inflammatory and autoimmune diseases such as rheumatoid arthritis, lupus, or Crohn's disease.

Despite the long-standing need for a vaccine against *Pneumocystis* or other fungal pathogens, to our knowledge no fungal vaccine has yet reached Phase III clinical trials.

DISCLOSURE OF THE INVENTION

We have discovered a vaccine that promotes CD4+ T cell-independent (CD4IND) host defense mechanisms to defend against infection by *Pneumocystis* and other fungi. The vaccine may be used to prevent or to treat fungal infections, including but not limited to *Pneumocystis* spp. The novel vaccine can provide protective immunity, even for immunocompromised individuals with reduced levels of CD4+ T cells.

We used an animal model that mimics HIV-induced CD4+ T cell deficiency: a CD4-depleted mouse treated with GK1.5, which is a monoclonal antibody that causes 97% or greater depletion of CD4+ T cells in spleen, blood, thymus, and lung. We have shown that using CD40L as an adjuvant allows the generation of protective humoral immune responses, even in CD4-deficient patients. We identified immunodominant antigens, including Kex1, a subtilisin-like protease. Mice that were immunized with Kex1 cDNA via a DNA-adenovirus vaccine showed significant protection against PC challenge. Surprisingly, when the vaccine was administered with the molecular adjuvant CD40L, even mice with CD4+ T-cells could develop a substantial immune response. By contrast, without the CD40L adjuvant, there was a poor response in CD4+ T-cell deficient mice.

We have improved the Kex1 DNA vaccine by defining and isolating a smaller antigen, which we have named "mini-kexin." This antigen will confer protective immunity, especially (but not only) when administered with a CD40L adjuvant. The mini kexin motif represents a highly conserved segment across *Pneumocystis* spp., and homologs are expressed in other fungi. It thus may also provide some protection against infection by other *Pneumocystis* spp. or other fungi, although we have not yet specifically tested efficacy against other fungal species. Codon optimization is preferred to enhance the expression of mini kexin DNA in eukaryotic cells; preliminary studies suggest that vaccine efficacy is improved with the codon-optimized version.

We have also constructed recombinant adenoviruses whose DNA encodes mini-kexin. In preliminary studies these adenovirus-based vectors have shown greater efficacy and have provoked greater mucosal IgA and IgG2a responses in the lung, either as compared to DNA alone, or as compared to systemic boosting with adenovirus. In SIV-infected macaques we have examined both anti-Kex1 titers and the rate of PC lung infection, the latter as determined by nested PCR in BAL fluid. The animals that remained PCP-negative (as determined by PCR in BAL fluid) had mean serum anti-Kex1 Ab levels that were greater than those in PCP-positive monkeys.

CD40 ligand (CD40L) is expressed on activated CD4+ T cells. CD40L and is critical for host defense against PC as well as bacterial pneumonia. We have previously shown that bone-marrow derived dendritic cells (DCs) can be genetically engineered to express CD40L (using an EI-deleted adenovirus, AdCD40L), resulting in significant DC activation and maturation. The activated, mature DCs, when pulsed with PC or bacterial antigens, and then injected into mice, produce protective, antigen-specific IgG independently of CD4+ T cells. This strategy was protective against PC both in primary-vaccinated, CD4+ T cell-deficient mice, and also in CD4+ T cell-deficient mice receiving adoptive transfer of immune serum or CD 19+ cells from vaccinated mice. These results demonstrated the critical role of B cells in protecting against PC after DC vaccination. We have also observed that dendritic cell IL-23 (but not IL-12) is required for functional recall antibody responses to PC antigen challenge. DC-based vaccination can suffer from problems such as scalability, and the cost of producing patient-specific DC's. To try to avoid these problems we developed a prime boost vaccination platform that greatly enhanced protection against PC in CD4-depleted mice, using the immunodominant antigen from PC, Kexin, and CD40L as a molecular adjuvant. Both components were required for vaccine efficacy in CD4-deficient hosts; however, the vaccine only resulted in a 3-log reduction of organism burden and thus did not afford complete protection.

We then undertook approaches to improve the effectiveness of the kexin DNA vaccine. One was to use antibody response to map regions of kexin that were particularly immunogenic. We call this 100 amino acid region "mini Kexin." The strategy was to perform mucosal boosting rather than systemic boosting. In preliminary studies, we found that mucosal boosting with a recombinant adenovirus encoding mini Kexin afforded significant greater protection against PC challenge as compared to systemic boosting.

We discovered that activation of CD40 signaling in vivo, in conjunction with vaccination with miniKexin, can produce antigen-specific immune responses, even in the absence of CD4+ T-cells. We have further discovered that mucosal boosting can provide effective vaccination against PCP, even in the absence of CD4+ T-cells.

In one aspect, the vaccine is used for therapeutic purposes in early HIV infection, when CD4 numbers remain intact, or it is used in otherwise immunocompetent hosts who are at risk for infection (e.g., patients with COPD, cystic fibrosis, or interstitial lung disease). In another aspect, vaccination is administered to individuals with advanced HIV infection, or to other immunosuppressed patients having low numbers of circulating CD4+ T-lymphocytes, to provide protective immunity.

MODES FOR PRACTICING THE INVENTION

Figure 1:
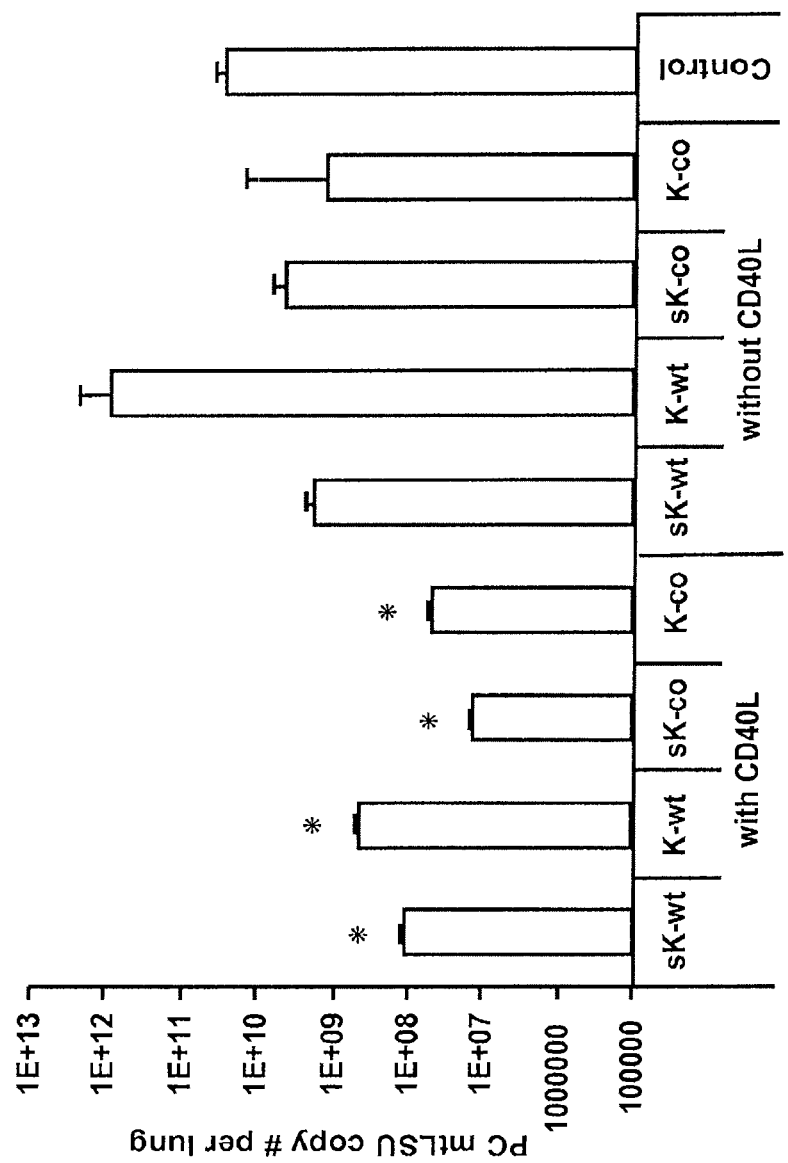
FIG. 1 depicts PC burden in mice receiving various vaccines, both with and without CD40L.

Preferably, the vaccine comprises a live recombinant delivery system, such as a bacterium or virus expressing mycobacteria genes, or an immunogenic delivery system such as a DNA vaccine, e.g. a plasmid, expressing one or more genes or gene fragments for mini-Kexin. Alternatively, the vaccine may comprise a protein vaccine, that is, the mini-Kexin polypeptide itself or a portion thereof, in a delivery system including a carrier or an adjuvant.

In one embodiment, one aspect of the invention is an isolated nucleic acid, preferably DNA, wherein said isolated nucleic acid:
(a) comprises a sequence that encodes mini-Kexin or a portion thereof, or comprises a sequence complementary thereto; but does not encode the entire Kexin protein; or
(b) has a length of at least 10 nucleotides, and preferably at least 20 nucleotides, and hybridizes readily under stringent hybridization conditions with a nucleotide sequence as disclosed herein, or with a nucleotide sequence selected from a sequence described in part (a) above.

Another embodiment comprises such a nucleic acid fragment inserted into a vector. The vector-based vaccine causes in vivo expression of mini-Kexin or a portion thereof by a human or other mammal to whom the vaccine has been administered, the amount of expressed antigen being effective to confer substantially increased resistance to a pathogenic fungus such as *Pneumocystis*.

Another embodiment of a vaccine for immunizing a human or other mammal against a pathogenic fungus such as *Pneumocystis* comprises as the effective component a non-pathogenic microorganism, wherein at least one copy of a DNA fragment comprising a DNA sequence encoding mini-Kexin or a portion thereof has been incorporated into the microorganism (e.g., placed on a plasmid or in the genome) in a manner allowing the microorganism to express, and optionally to secrete mini-Kexin or a portion thereof.

Another embodiment comprises a replicable expression vector that comprises a nucleic acid fragment according to the invention, and a transformed cell harboring at least one such vector.

Another embodiment comprises a method for immunizing a mammal, including a human being, against a pathogenic fungus such as *Pneumocystis*, comprising administering to the mammal an effective amount of a vaccine a nucleic acid, a polypeptide, a vector, or a cell as described.

A further embodiment comprises a pharmaceutical composition that comprises an immunologically reactive amount of at least one member selected from the group consisting of:
(a) the mini-Kexin polypeptide, or an immunogenic portion thereof;
(b) a polypeptide whose amino acid sequence has an identity of at least 70%, 75%, 80%, 85%, 90%, or 95% to anyone of said polypeptides in Cal; and is immunogenic;
(c) a fusion polypeptide comprising at least one polypeptide according to (a) or (b) and at least one fusion partner;
(d) a nucleic acid that encodes a polypeptide according to Cal, (b) or (c);
(e) a nucleic acid whose sequence is complementary to the sequence of a nucleic acid according to (d);
(f) a nucleic acid sequence having a length of at least 10 nucleotides, or at least 20 nucleotides, that hybridizes under stringent conditions with a nucleic acid according to (d) or (e); and
(g) a non-pathogenic micro-organism that has incorporated therein (e.g. placed in a plasmid or chromosome) a nucleic acid sequence according to (d), (e), or
(f) in a manner to permit expression of the encoded polypeptide.

A further embodiment comprises a method for stimulating an immunogenic response in an human or other mammal by administering to the human or other mammal an effective amount of at least one member selected from the group consisting of:
(a) the mini-Kexin polypeptide, or an immunogenic portion thereof;
(b) a polypeptide whose amino acid sequence has an identity of at least 70%, 75%, 80%, 85%, 90%, or 95% to anyone of said polypeptides in Cal; and is immunogenic;
(c) a fusion polypeptide comprising at least one polypeptide according to (a) or (b) and at least one fusion partner;
(d) a nucleic acid that encodes a polypeptide according to (a), (b) or (c); (e) a nucleic acid whose sequence is complementary to the sequence of a nucleic acid according to (d);
(f) a nucleic acid sequence having a length of at least 10 nucleotides, or at least 20 nucleotides, that hybridizes under stringent conditions with a nucleic acid according to (d) or (e); and
(g) a non-pathogenic micro-organism that has incorporated therein (e.g. placed in a plasmid or chromosome) a nucleic acid sequence according to (d), (e), or
(f) in a manner to permit expression of the encoded polypeptide.

Definitions. Unless context clearly indicates otherwise, the following definitions should be understood to apply throughout the specification and claims. Other terms, those for which specific definitions are not given, should be interpreted as they would be understood, in context, by a person of skill in the art:

The word "polypeptide" or "protein" or "peptide" should have its usual meaning: an amino acid chain of any length, including a full-length protein, oligopeptide, short peptide, or fragment thereof, wherein the amino acid residues are linked by covalent peptide bonds. As used in the present specification and claims, unless context clearly indicates otherwise, no distinction is intended between the terms "polypeptide," "peptide," and "protein," which should be considered synonymous.

The polypeptide may be chemically modified by being glycosylated, phosphorylated, lipidated, by incorporating one or more prosthetic groups or functional group, or by containing additional amino acids such as e.g. a his tag or a signal sequence.

Each polypeptide may thus be characterized by specific amino acids and be encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and are still immunogenic. Substitutions are preferably conservative.

A "substantially pure polypeptide fragment" means a polypeptide preparation that contains at most 5% by weight of other polypeptide material (lower percentages of other polypeptide material are preferred, e.g. at most 4%, at most 3%, at most 2%, at most 1%, and at most ½%). It is preferred that the substantially pure polypeptide is at least 96% pure, i.e. that the specified polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is in "essentially pure form", i.e. that the polypeptide fragment is essentially free of any other antigen with which it is natively associated, i.e. essentially free of any other antigen from the same fungus. This can be accomplished by preparing the polypeptide fragment by means of recombinant methods in a non-fungal host cell, or by synthesizing the polypeptide fragment by the well-known methods of solid or liquid phase peptide synthesis, e.g. by the method described by Merrifield or variations thereof.

The term "nucleic acid fragment" (or "nucleic acid sequence") means any nucleic acid molecule including DNA, RNA, LNA (locked nucleic acids), PNA, RNA, dsRNA and RNA-DNA-hybrids. A preferred nucleic acid for use in this invention is DNA. Also included are nucleic acid molecules comprising non-naturally occurring nucleosides. The term includes nucleic acid molecules of any length, e.g. from 10 to 10,000 nucleotides, depending on the use and context. The nucleic acid molecule is optionally inserted into a vector.

The term "stringent" when used in conjunction with hybridization conditions has the meaning generally understood in the art, i.e. the hybridization is performed at a temperature not more than 15-20° C. under the melting point T m, cf. Sambrook et al., 1989, pages 11.45-11.49. Preferably, the conditions are "highly stringent", i.e. 5-10° C. under the melting point Tm.

The term "sequence identity" indicates a quantitative measure of the degree of homology between two amino acid sequences of equal length or between two nucleotide sequences of equal length. The two sequences to be compared are aligned to the best possible fit, allowing for the insertion of gaps or alternatively, for truncation at one or both ends. The sequence identity can be calculated as $(N_{ref}-N_{dif})100/N_{ref}$, wherein $N_{dif}$ is the total number of non-identical residues in the two sequences when aligned, and wherein $N_{ref}$ is the number of residues in one of the sequences. Hence, the DNA sequence AGTCAGTC (SEQ ID NO: 5) has a sequence identity of 75% with the sequence AATCAATC (SEQ ID NO: 6) ($N_{dif}=2$ and $N_{ref}=8$). A gap is counted as non-identity of the specific residue(s),i.e., the DNA sequence AGTGTC (SEQ ID NO: 7) has a sequence identity of 75% with the DNA sequence AGTCAGTC (SEQ ID NO: 5) ($N_{dif}=2$ and $N_{ref}=8$). Sequence identity can alternatively be calculated by available software, such as the sequence alignment program BLAST®, e.g. the protein alignment BLASTP® program (Pearson, 1988). Alignment may also be performed with the sequence alignment method CLUSTALW™ with default parameters.

A preferred minimum percentage of sequence identity is at least 80%, such as at least 85%, at least 90%, at least 91%, at least 92%, at least 93%, at least 94%, at least 95%, at least 96%, at least 97%, at least 98%, at least 99%, and at least 99.5%

"Variants." A common feature of the polypeptides of the invention is their capability to induce an immunological response. It is understood that a variant of mini-Kexin produced by substitution, insertion, addition or deletion may also be immunogenic as determined by any of the assays described herein.

An "immune individual" is a human or other mammal who has cleared or controlled an infection with a virulent fungus such as *Pneumocystis*, or who has received a vaccination in accordance with this invention.

The "immune response" of an individual may be monitored by anyone of several methods known in the art, including for example one or more of the following:

A cellular response may be determined in vitro by induction of the release of a relevant cytokine such as IFN-gamma from, or the induction of proliferation in lymphocytes withdrawn from a human or other mammal currently or previously infected—with virulent fungus or directly or indirectly immunized with polypeptide. The induction may be performed by the addition of the polypeptide or an immunogenic portion of the polypeptide to a suspension comprising from $2\times10^5$ cells to $4\times10^5$ cells per well. The cells are isolated from blood, the spleen, the liver, or the lung, and the addition of the polypeptide or the immunogenic portion results in a concentration of not more than 20 g per ml in suspension, with the stimulation being performed over a period from two to five days. To monitor cell proliferation the cells are pulsed with radioactively-labeled thymidine; after 16-22 hours of incubation liquid scintillation counting is used to assess proliferation. A positive response is considered to be one that exceeds background by at least two standard deviations. The release of IFN-gamma can be determined, e.g., by the ELISA method, or other methods known in the art. Other cytokines besides IFN-gamma may be used to assess immunological response to the polypeptide, such as IL-12, TNF-alpha, IL-4, IL-5, IL-10, IL-6, or TGF-beta. A sensitive method for detecting an immune response is the ELISpot method for determining the frequency of IFN-gamma producing cells. In an ELIspot plate (MAHA, Millipore) that is pre-coated with anti-murine IFN-gamma antibodies (PharMingen), graded numbers of cells isolated from blood, spleen, or lung (typically from I to $4\times10^5$ cells/well) are incubated for 24-32 hrs in the presence of the polypeptide or an immunogenic portion therefor, at a concentration not more than about 20 g per ml. The plates are subsequently incubated with biotinylated anti-IFN-gamma antibodies followed by a streptavidin-alkaline phosphatase incubation. The cells producing IFN-gamma are identified by adding BCIPINBT (Sigma), and the relevant substrates develop spots. These spots can be enumerated with a dissection microscope. It is also possible to determine the presence of mRNA that encodes the relevant cytokine by PCR. Usually one or more cytokines will be measured using, for example, PCR, ELISPOT, or ELISA. It will be appreciated by a person skilled in the art that the immunological activity of a particular polypeptide can be evaluated by observing whether there is a significant increase or decrease in the amounts of these cytokines.

A cellular response may also be determined in vitro with T cell lines derived from an immune individual, or a *Pneumocystis*-infected person, where the T cell lines have been driven with either live fungus, extracts from the fungus, or culture filtrate for 10 to 20 days, with the addition of IL-2. The induction is performed by adding not more than 20 g polypeptide per ml suspension to the T cell lines, from $1\times10^5$ cells to $3\times10^5$ cells per well, with incubation from two to six days. The induction of IFN-gamma or the release of another relevant cytokine is detected by ELISA. The stimulation of T cells can also be monitored by detecting cell proliferation using radioactively labeled thymidine as described above. For both assays a positive response is considered to be one that is at least two standard deviations above background.

A humoral response may be determined in vitro by a specific antibody response from an immune or infected individual. The presence of antibodies may be determined through methods known in the art, e.g., by ELISA or Western blot. The serum is preferably diluted in PBS from 1:10 to 1:100 and added to the adsorbed polypeptide, with incubation from 1 to 12 hours. By the use of labeled secondary antibodies the presence of specific antibodies can be determined by measuring the OD, e.g. by ELISA, where a positive response is considered to be one that is at least two standard deviations above background, or alternatively by a visible response in a Western blot.

Protein Vaccine. Another aspect of the invention pertains to a vaccine composition comprising the mini-Kexin polypeptide, or an immunogenic portion thereof, or a fusion polypeptide thereof. It is preferred that the vaccine additionally comprise an immunologically and pharmaceutically acceptable carrier, vehicle or adjuvant.

Suitable carriers for polypeptides may be selected from the group consisting of a polymer to which the polypeptides are bound by a hydrophobic, non-covalent interaction, such as a polystyrene, or a polymer to which the polypeptides are covalently bound, such as a polysaccharide, or a polypeptide, e.g. bovine serum albumin, ovalbumin, or keyhole limpet haemocyanin. Suitable vehicles may be selected from the group consisting of a diluent and a suspending agent. The adjuvant is preferably selected from the group consisting of dimethyldioctadecylammonium bromide (DDA), Quil A, poly I:C, aluminum hydroxide, Freund's incomplete adjuvant, IFN-gamma, IL-2, IL-12, monophosphoryllipid A (MPL), Trehalose Dimycolate (TDM), Trehalose Dibehenate, and muramyl dipeptide (MDP).

The preparation of vaccines that contain polypeptides as their active ingredients is generally well understood in the art, as exemplified by U.S. Pat. Nos. 4,608,251; 4,601,903; 4,599,231 and 4,599,230, and published application US2004/0057963, the complete disclosures of all of which are incorporated herein by reference.

Other methods of achieving adjuvant effect for a vaccine include the use of agents such as aluminum hydroxide or aluminum phosphate (alum), synthetic (Carbopol), aggregation of the polypeptide in the vaccine by heat treatment, aggregation by reactivating with pepsin-treated (Fab) antibodies to albumin, mixture with bacterial cells such as *C. parvum* or endotoxins or other lipopolysaccharide components of gram negative bacteria, emulsion in physiologically acceptable oil vehicles such as mannide mono-oleate (Aracel A), or emulsion with 20 percent solution of a perfluorocarbon (Fluosol-DA) used as a block substitute. Other possibilities involve the use of immune-modulating substances such as cytokines or synthetic IFN-gamma inducers such as poly I:C in combination with an adjuvant Another possibility for achieving adjuvant effect is to conjugate the polypeptide or a portion thereof to an antibody (or antigen binding antibody fragment) against the F cy receptors on monocytes/macrophages.

The vaccines are administered in a manner that is compatible with the dosage formulation, and in an effective, immunogenic amount. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg, as may readily be determined by routine experimentation such as is well known in the art. Suitable regimens for initial administration and booster shots are also variable but are typified by an initial administration followed by subsequent inoculations or other administrations.

As used in the specification and claims, an "effective amount" or an "effective dosage" of a vaccine is an amount or dosage, that when administered to a patient (whether as a single dose or as part of a multi-dose or boosting regimen) provides protective immunity to a clinically significant degree; or alternatively, to a statistically significant degree as compared to control. "Statistical significance" means significance at the P<0.05 level, or such other measure of statistical significance as would be used by those of skill in the art of biomedical statistics in the context of immunization.

The manner of application may be varied. Any of the conventional methods for administration of a vaccine are applicable. These can include oral application on a solid physiologically acceptable base or in a physiologically acceptable dispersion, parenterally, by inhalation, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations and inhalable aerosols. For Suppositories, traditional binders and carriers may include, for example, polyalkyene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions may take the form of solutions, suspensions, tablets, pills, capsules, sustained release formulations or powders and advantageously contain 10-95% of active ingredient, preferably 25-70%.

DNA Vaccine. In a preferred embodiment, nucleic acid fragments in accordance with the invention are used for the in vivo expression of antigens, i.e. in so-called DNA vaccines as reviewed in Ulmer et al 1993, which is incorporated by reference. Hence, the invention also relates to a vaccine comprising a nucleic acid fragment according to the invention, the vaccine causing in vivo expression of antigen by a human or other mammal, the amount of expressed antigen being effective to confer substantially increased resistance to infections caused by virulent fungi, including for example *Pneumocystis jerovici* or other *Pneumocystis* spp.

Live Recombinant Vaccines; Plasmids. Another possibility for effectively activating a cellular immune response is to express the antigen in a non-pathogenic microorganism or virus that is then used as a vaccine. Well-known examples of such microorganisms are *Mycobacterium bovis* BCG, *Salmonella*, and *Pseudomonas*, and examples of such viruses are Vaccinia Virus and Adenovirus.

Accordingly, another aspect of the present invention is to incorporate one or more copies of a DNA sequence as described into the genome of the microorganism or virus in a manner allowing the micro-organism to express and secrete the polypeptide. The incorporation of more than one copy of a nucleotide sequence of the invention may enhance the immune response.

Another possibility is to integrate the DNA encoding the polypeptide in an attenuated virus such as the vaccinia virus or Adenovirus (Rolph et al 1997). The genes carried by the recombinant vaccinia virus are expressed within an infected host cell, and the expressed polypeptide of interest can induce an immune response.

Because the target population for this vaccine will often have a compromised immune system, even attenuated live vaccines may be inappropriate vehicles. In such cases, it can be preferred to administer the DNA sequence in a non-replicating vehicle, such as a plasmid or a disabled virus that

Example 1

Co-administration of CD40L with mini-Kexin vaccination induces a CD4JND humoral response and protection against PC in vivo. Four forms of mini-Kexin DNA are used for vaccination: mini-Kexin-wild type (mKexin-WT); mini-Kexin that has been codon optimized for mammalian expression (mKexin-CO); miniKexin that has been engineered to be secreted with an IgGC leader sequence (sm-Kexin); and smKexin that has been codon optimized (sm-Kexin-CO). We compared these wild type and •codon-optimized forms of the DNA vaccine. We also compare mucosal boosting with recombinant adenovirus and recombinant modified vaccinia Ankara strain (MVA) vectors. Outcome measures include anti-Kexin and anti-PC isotype-specific antibody responses, as well as anti-Kexin subclass determinations. Serum is tested in functional assays including opsonic phagocytosis, and passive transfer protection into scid mice. We also examine the efficacy of the vaccine against PC challenge performed at several times after vaccination.

Example 2

Our hypothesized mechanism predicts that endogenous IL-23 is required; and results in durable vaccine responses in both CD4+ T-cell deficient mice and CD40L knockout mice. Specifically we demonstrate the efficacy of CD40L co-transduction in CD40L knockout mice; and the requirement of IL-12 family members (including IL-I2p35, IL-I2p40, and IL-23), and critical activation molecules that are induced by CD40L-modified DCs to generate effective primary and memory B-cell responses. Preliminary studies have suggested that 11-23 production is critical to generate B-cell memory against PC antigen.

Example 3

CD4IND pathogen-specific immune responses against *Pneumocystis* kexin are generated in an SIV model of immunodeficiency in macaques. We expect that the mini-kexin constructs will produce vaccine-induced immune responses in SIV-infected, CD4 deficient macaques. Control or SIV infected macaques will undergo DNA priming, followed by mucosal boosting 4 weeks after mock or live SIV infection. Outcome measures will include humoral responses to the vaccine, and the prevention of *Pneumocystis* colonization as determined by PCR of BAL fluid. We will also challenge SIV-infected monkeys with live *Pneumocystis*, and demonstrate vaccine efficacy in the challenge model.

Example 4

We generated anti-*Pneumocystis* antibodies in CD4-deficient mice by vaccination with PC-pulsed, CD401-transduced, bone marrow-derived dendritic cells. These antibodies stain the surface of PC, and enhance opsonic phagocytosis and killing of PC in a dectin-1-independent but Fc-dependent manner. These antibodies also confer significant protection against PC when passively transferred to scid mice prior to PC challenge.

Example 5

We identified antigen specificities using both I-dimensional and 2-dimensional electrophoresis, as well as immunoprecipitation followed by 2-D gel electrophoresis. Silver-stained spots on 2-D gels were picked, enzymatically-digested, and analyzed by tandem MS (Applied Biosystems). We also performed N-terminal sequencing on proteins. Due to a lack of published data for the entire PC genome, and in light of the significant homology of many PC genes to those of *Saccharomyces cerevisiae* and *S. pombe*, we performed homology searches against PC and *Saccharomyces* spp. One antigen consistently identified by both MS-MS and N-terminal sequencing was kexin (also called Kex1). Kex I is a protease with high homology to furin. Kexin is presumably involved in processing of pre-pro proteins in yeast. Monoclonal antibodies raised against Kex1 show protective efficacy in murine models of PCP.

Example 6

We cloned the full length Kex1 cDNA, and generated DNA vaccines, both with and without an additional open reading frame encoding CD40L as a B-cell adjuvant CD4-deficient mice that were immunized by intramuscular DNA encoding Kex1 and CD40L developed significant anti-*Pneumocystis* antibody titers, as well as approximately a three log protection against PC challenge. Moreover these antibodies stained the surface of PC organisms from mouse and monkey, and enhanced opsonic phagocytosis and killing of mouse PC in vitro. However, despite the efficacy of full-length Kex 1 vaccination, vaccinated mice still had readily detectable infection 4 and 6 weeks after challenge.

Example 7

To improve upon our original Kex1 vaccine we tried several approaches. The first was to examine if mucosal boosting with recombinant adenovirus would enhance DNA priming. Although full-length Kex1 could be packaged, the recombinant Ad5-based vectors grew poorly, with titers of $10^7$ or $10^8$ per ml. The Kex1 coding sequence is over 3 kB. We explored whether we could improve both packaging and expression by truncating the antigen and by using codon optimization. Our analysis of Kex 1 revealed a 100 amino acid segment of Kex1 with over 75% homology among PC organisms obtained from mouse, rat, monkey, and human hosts. (See Figure I from Priority application 61/294,252, not reproduced here but incorporated by reference.)

Example 9

We next performed passive transfer experiments into scid mice using control serum, serum from Kexin/CD40L vaccinated mice, and serum from vaccinated mice that had been pre-adsorbed against recombinant Kexin. The mice were then challenged with PC (2×IOS cysts) intratracheally. Mice were sacrificed at day 28, and PC burden in the lung was assessed by real-time PCR. Transfer of 300 μl of serum from Kexin/CD40L-vaccinated mice resulted in significantly reduced PC burden as compared to control serum. Adsorption of serum against recombinant Kexin significantly attenuated the protection of the transferred serum. (See FIG. 3 from priority application 61/294,252, not reproduced here but incorporated by reference.)

Example 10

We modified the vaccine by constructing vectors encoding the 100 amino acid conserved region of Kex 1 that we identified, a region that we have named "mini-Kexin." We constructed 4 DNA vaccines: (1) wild-type mini Kexin without a leader sequence, (2) wild type mini Kexin with an IgGk leader sequence to facilitate secretion, (3) codon-optimized mini Kexin with no leader sequence, and (4) codon optimized mini Kexin with a IgGk leader sequence. These vectors were called, respectively: (1) pmini-Kexin WT, (2) psec-mini-Kexin-WT, (3) pmini-Kexin CO, and (4) psec-mini-Kexin-CO. To assess the secretion of mini-Kexin we transfected 293 cells with these constructs and assayed for Kexin by direct ELISA in cell lysates or in cell supernatants 48 hours after transfection. (See FIG. 4 from priority application 61/294,252, not reproduced here but incorporated by reference.) The addition of the IgG-kappa leader sequence in the psec-mini Kexin constructs resulted in higher levels of Kexin in cell supernatants. Moreover, codon optimization was associated with higher expression. Thus a preferred embodiment uses both a leader sequence and codon optimization.

Example 12

To test the protective effect of the antibodies against PC infection, we performed a PC challenge following the second dose of DNA. The mice were sacrificed 28 days later to assess PC organism burden in lung tissue (FIG. 1). Mice vaccinated with psec-kexin-Co-CD40L had the lowest organism burden in the lung compared to all other groups ($*p<0.01$ ANOVA, n=6 per group). Furthermore, the addition of CD40L was associated with lower organism burdens in all vaccine groups compared to mice vaccinated without CD40L. Nevertheless, there were still between $10^6$ and $10^7$ PC organisms present, even in the psec-kexin-Co-CD40L group.

Example 13

Figure 2:
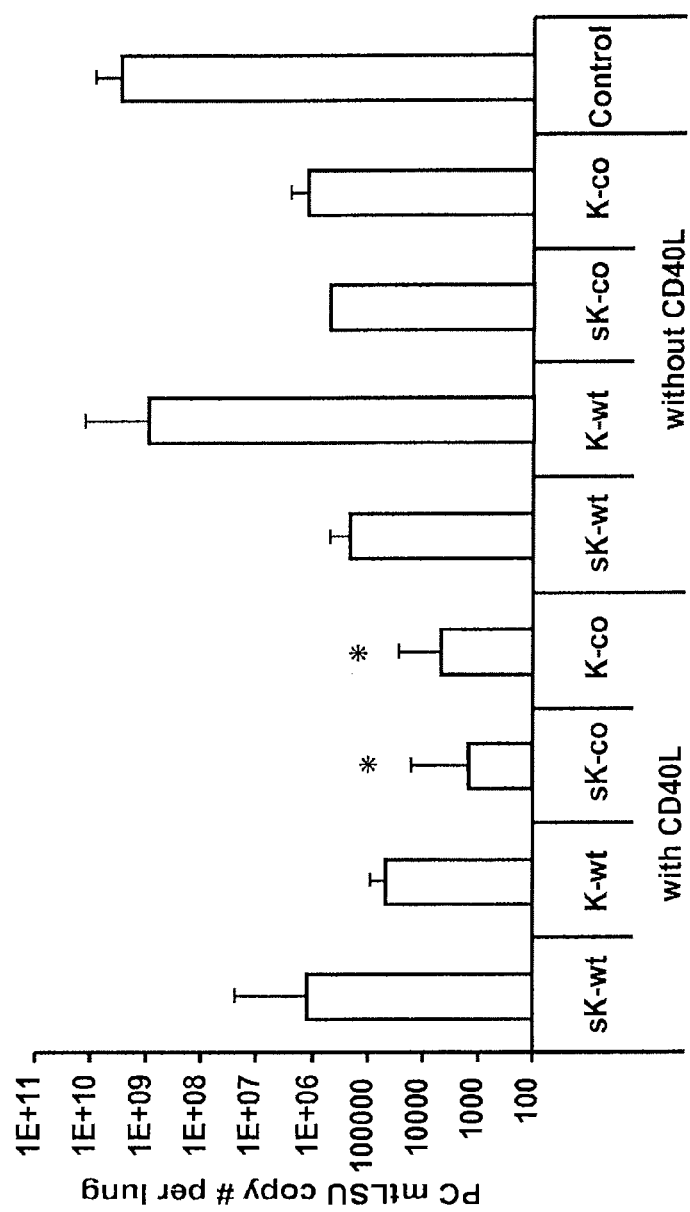
FIG. 2 depicts PC copy number in the lung 28 days after PC challenge in mice receiving various vaccines, both with and without CD40L.

We examined whether mucosal boosting can augment protection against PC. We constructed recombinant AdS-based vectors encoding all four of the mini-Kexin constructs described above. Mice were primed with 2 IM injections of DNA, followed either by no mucosal boost or by intranasal boosting with $10^7$ PFU of AdS encoding the same construct as was used for the DNA prime vaccination. FIG. 2 depicts PC copy number in the lung 28 days after PC challenge in these mice. The mucosal boost with AdCD40L resulted in nearly a three log improvement in both the sK-co and k-Co groups ($p<0.01$ ANOVA, n=6 per group, compared to SK-wt or K-wt with CD40L).

Example 14

Figure 3:
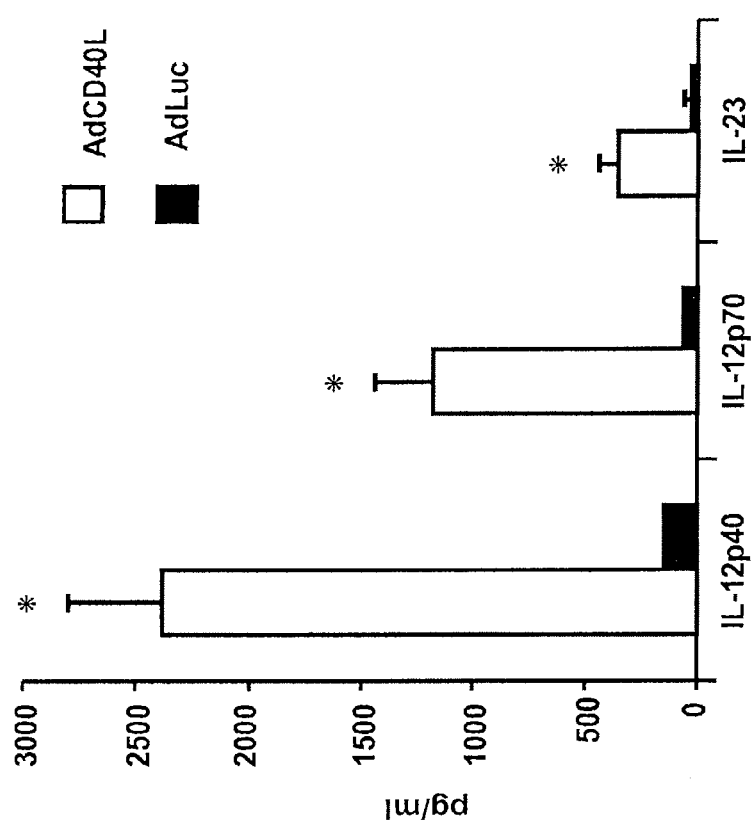
FIG. 3 depicts the induction of IL-12p40, IL-12p70, and IL-23 in mice transduced with AdCD40L, versus controls.

Our hypothesis predicts that this strategy: (1) should require endogenous IL-23, and (2) should result in durable vaccine responses both in CD4+ T-cell deficient mice and in CD40L knockout mice. We have demonstrated that AdCd40L is a potent inducer of IL-12p40, IL-12p70, and IL-23 (FIG. 3). For these experiments, bone marrow-derived dendritic cells were grown from hematopoietic progenitors, and transduced with AdLuc or AdCD40L at a dose of 100 viral particles per cell. Supernatants were collected 24 hours later and assayed for IL-12p40 or IL-12p70 by a high throughput immunoassay, LUMINEX®, or for IL-23 by ELISA (n=5 per group, * denotes $p<0.05$ compared to AdLuc controls).

Example 15

Figure 4A:
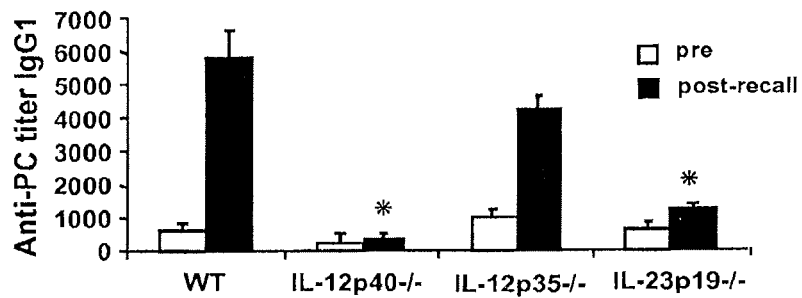
FIGS. 4A-4C depict, respectively, anti-PC IgG I titers, anti-PC IgG2 titers, and percent killing of PC organisms by anti-PC serum in response to vaccination with various DCs.
Figure 4B:
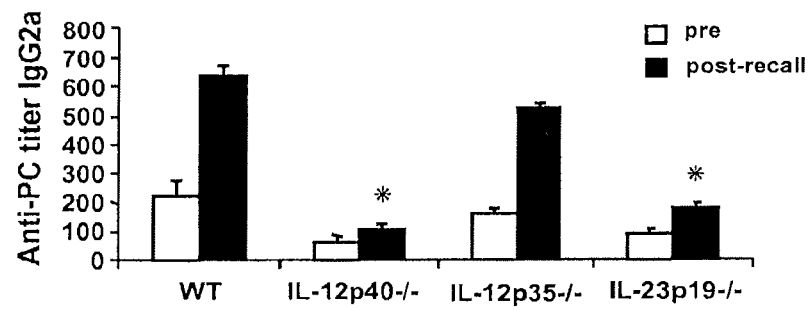
Figure 4C:
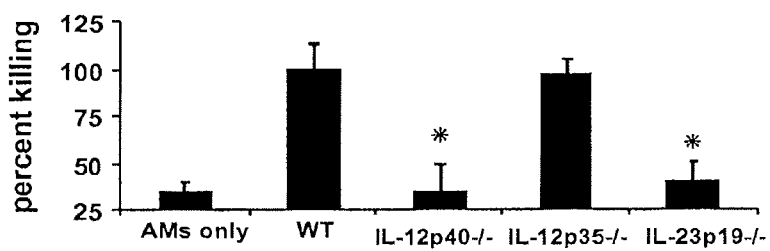

To determine the role of IL-12 and IL-23 in AdCD40L-transduced, DC-based vaccine responses, we generated DCs from IL-12p40-1-, IL-12p35-1-, or IL-23p19.1-mice; transduced each DC genotype with AdCD40L; pulsed the DCs with PC antigen; and then administered the DCs intravenously to CD4-depleted mice. Primary antibody responses were measured after 4 weeks. To assess recall responses, mice were re-challenged with PC antigen by IP injection, and serum antibody responses were measured 10 days later. As shown in FIG. 4A, primary IgG I responses were similar regardless of the DC expression of IL-12p40, IL-12p35, or IL-23p19. Mice vaccinated with IL-23-deficient Des (either IL-12p40-1- or IL-23p 19-1-DCs) had reduced primary IgG2a responses to PC (FIG. 4B). Furthermore, recall response to PC antigen, as a measure of B-cell memory, was significantly diminished both in IL-12p40-1- and in IL-23p19 deficient DCs, but not in IL-12p35-1-DCs (FIGS. 4A and 4B, * denotes $p<0.05$ as compared to the other groups, ANOVA, n=5-6 per group). These data demonstrated that IL-23 is an important mediator of CD40L-induced B cell expansion and antigen-specific recall responses. The defect in functional B-cell memory was also associated with diminished opsonic killing activity of anti-PC serum from CD4-depleted mice vaccinated with DCs from either IL-12p40/- or IL-23p 19-1-mice (FIG. 4C, * denotes $p<0.05$ compared to the other groups, ANOVA, n=5-6 per group).

Example 16

CD4IND, pathogen-specific immune responses against *Pneumocystis* kexin are produced in an SIV model of immunodeficiency in macaques. We have assessed spontaneous PC infection in macaques infected with SIV/Delta B670. CD4 counts below 500 cells/µL have been strongly associated with an increase in PC colonization in the lung, as assessed by nested PCR in BAL fluid. Five of five SIV-infected monkeys developed detectable PC colonization, as assayed by nested PCR. Interestingly, several monkeys had an initial increase in anti-Kexin antibody titers, followed by a fall in titers prior to the development of a positive PCR response for pc. In a second cohort of animals, preliminary studies suggested that SIV-infected monkeys with high baseline anti-Kex1 titers were protected against PC infection, as measured by PCR in BAL. We will determine the rate of PC infection at necropsy in 25 SIV-infected and 25 non-SIV-infected macaques. For these studies we will assess PC colonization by nested PCR, and real-time PCR on lung tissue and BAL. These data will also be compared to standard histological detection of PC by GMS staining of lung tissue.

Example 17

Additional studies confirm that CD 40L co-administration results in CD41ND immune responses after 1M DNA vaccination, through B-cell responses. Our preliminary results suggest that codon-optimized, secreted antigen is a better driver of the B cell response as compared to non-secreted or wild-type forms of Kexin. We have cloned the kexin constructs and CD40L into pBUDCE4.1 (Invitrogen), which contains two expression cassettes (one driven by CMV and one driven by the human EF-1 alpha promoter), allowing both genes to be effectively expressed in transduced cells.

Example 18

Experimental Groups. Male 6-8 week old BALB/C mice will be CD4-depleted by the administration of 0.3 mg GK1.5

IP by weekly injection, or given rat IgG as a control. 48 hours later, mice will be randomized to be vaccinated by the 1M injection of pmini-Kexin WT, psec-mini-Kexin-WT, pmini-Kexin CO, or psec-mini-Kexin-CO; and in each case, either with or without CD40L. One group of mice will be injected with pBudCD40L with no PC antigen as a control. Sample size will be 10 mice per group, which should give sufficient statistical resolution to detect a ~30% difference in anti-PC or Kexin IgG between different routes of vaccination.

Manipulations: There will be two doses of plasmid injections, three weeks apart.

Measures and Outcomes: Sera will be assayed for anti-PC and anti-Kexin antibodies, both IgM and IgG, by ELISA at 3, 6, and 9 weeks. Isotypes will be determined by using appropriate anti-mouse IgG isotypes: IgG1, IgG2a, IgG2b, IgG3 (Pierce, Rockford, Ill.). At 9 weeks, mice will be sacrificed and lungs will be lavaged for anti-PC and anti-Kexin IgA levels. Kexin-specific, IgG-expressing B cells in the spleen and mediastinal lymph nodes will be assayed by Elispot. Serum antibodies will also be tested for complement-dependent killing, and for opsonic phagocytosis and killing of PC in vitro. Briefly, serial dilutions of sera will be incubated with PC cysts and cultured in RPM1640+10% FCS (with or without heat inactivation) for 24 hours, followed by assessment of PC mtLSU rRNA integrity by real-time PCR. To assess macrophage-dependent killing the assay is performed in the presence of 50,000 alveolar macrophages obtained by lung lavage. If we observe high antibody titers and augmentation of PC killing in vitro, we will also perform passive transfer experiments in scid mice with 300 µl of serum, followed by pulmonary PC challenge. Scid mice will be sacrificed 28 days later to determine if the passive transfer of serum prevents PC infection.

Expected Results and Interpretations: We expect to observe significant induction of anti-PC and anti-Kexin IgG in CD4-depleted mice vaccinated with pmini-Kexin WT, psec-mini-Kexin-WT, pmini-Kexin CO, or psec-mini-Kexin-CO-particularly when CD40L is included in the plasmid. We also expect that CD40L will be required for efficient 19A production in BAL in these mice. Our preliminary data also suggest that IgG levels, and perhaps Kexin-specific IgG- and IgA-producing B-cells are enhanced in the secreted Kexin1 codon optimized, CD40L groups in the spleen. We expect the precursor frequency to be significantly lower in the mediastinal lymph nodes as compared to spleen in this stage of the vaccine. We also expect to observe vaccine-induced increases in opsonic activity and killing of PC in vitro, as well as protection in passive transfer experiments.

Alternative Approaches: We expect to observe a mixed TH1 and TH2 antibody response, since IL-4 has been reported to have synergy with IL-12 p70 and CD40L in activating B-cells to a TH2 response. Alternatively, activated DC's have been shown to induce preferential TH1 responses in B-cells. Thus we will observe the roles of specific endogenous cytokines such as IL-12, IL-23, in IL-12p40, IL-12p35, and IL-23 knockout mice. If we observe only a modest anti PC/Kexin IgG response in the IM regimen, we will investigate electroporation after DNA administration. Electroporation enhances CD8+ T-cell responses. Its effect on humoral immune response is unclear, but and we are already achieving significant B-cell responses, and therefore see electroporation as being less preferred. The titer or half life of the antibody in the scid mice will be confirmed by measuring the titer both immediately after transfer and on day 28. Prior studies with DC-based vaccines suggest that 300 µl of serum should provide sufficient Ab to protect during the 28 day study period.

Example 19

The effect of mucosal boosting with recombinant adenovirus virus-based vectors following DNA priming.

Hypothesis: We hypothesize that the co-administration of CD40L with antigen allows for CD4-independent (CD4IND) B-cell responses in vivo, and that mucosal boosting will enhance mucosal antigen-specific B-cell responses, as well as overall protective immunity.

Rationale: Preliminary studies have demonstrated that CD40L co-administered with Kexin antigen resulted in CD4IND B-cell responses. To optimize the in vivo response, we postulate that mucosal boosting with recombinant adenovirus vectors will enhance mucosal IgA and IgG B-cell responses.

Experimental Groups. Male 6.8 week old BALBC mice will be CD4·depleted by the administration of 0.3 mg GK1.5 IP by weekly injection or given rat IgG as a control for the CD4-replete group. 48 hours later, mice will be randomized to be vaccinated by the 1M injection of pmini-Kexin WT, psec-mini-Kexin-WT, pmini-Kexin CO, or psec-mini-Kexin-CO, in each case with or without CD40L. One group of mice will be injected with pBudCD40L with no PC antigen as a control. After 6 weeks mice will be further randomized for mucosal boosting with $10^7$ adenovirus encoding the same antigen construct as the prime vaccination, with or without an equal dose of AdCD40L. Sample sizes will be 10 mice per group, to give the statistical resolution to detect a 30% difference in anti-PC or Kexin IgG between different routes of vaccination.

Manipulations: Plasmid injections will be repeated every three weeks for two doses as otherwise previously described by Ramsay et al. We will administer $10^7$ of E1-deleted, Ad5-based vectors encoding antigen, with or without AdCD40L by intranasal administration.

Measures and Outcomes: Sera will be assayed for anti-PC and anti-Kexin 19M, and IgG isotypes by ELISA at 3, 6, and 9 weeks using appropriate anti-mouse IgG isotypes: IgG1, IgG2a, IgG2b, IgG3 (pierce, Rockford, Ill.). At 9 weeks, mice will be sacrificed and lungs will be lavaged for anti-PC and anti-Kexin IgA levels. B cells expressing Kexin-specific IgG and 19A in the spleen and mediastinal lymph nodes will be assayed by Elispot. Serum and BAL antibodies will also be tested for complement-dependent killing as well as opsonic phagocytosis and killing of PC in vitro. In brief, serial dilutions of sera will be incubated with PC cysts and cultured in RPM1640+10% FCS (with or without heat inactivation) for 24 hours, followed by assessment of PC mtLSU rRNA integrity by real-time PCR. To assess macrophage-dependent killing the assay is performed in the presence of 50,000 alveolar macrophages obtained by lung lavage. If we observe high titers of Ab and augmentation of PC killing in vitro, we will also perform passive transfer experiments in scid mice with 300 µl of serum followed by pulmonary PC challenge. Scid mice will be sacrificed 28 days later to determine if the passive transfer of serum prevents PC infection.

Expected Results and Interpretations: We expect to observe significant enhancement in both BAL anti-PC and anti-Kexin IgG and IgA in animals that are mucosally boosted as compared to those in Example 18. Moreover we expect to observe increases in Kexin-specific IgG and IgA B-cells in the mediastinal lymph nodes in Ad-boosted mice. We also expect that CD40L will be required in both the priming and the boosting regimen to achieve strong mucosal IgG and IgA anti-PC and anti-Kexin antibody responses. We also expect to observe vaccine-induced increases in opsonic activity and killing of PC in vitro, as well as protection in passive transfer experiments.

Alternative Approaches: The dosage of the boost will be optimized, following initial proof of concept The initial dose of $10^7$ has been validated in preliminary studies, but could be increased, e.g., to $10^8$ for both antigen-containing Ad as well as for AdCD40L. The titer and half life of the antibody in the scid mice will be assayed by measuring titer immediately after transfer and on day 28. Prior studies with DC-based vaccines suggest that 300 µl of serum should provide sufficient Ab to protect throughout the 28 day study period. The relative importance of mucosal Ab and serum Ab for protective immunity can also be assayed, e.g., by transferring concentrated BAL to supply 100 µl of protein. Controls will consist of BAL that is brought up to 100 µl of protein with naive mouse serum.

Example 20

The effect of mucosal boosting with recombinant adenovirus virus-based vectors after DNA priming in conferring protection against a PC challenge.

Hypothesis: We hypothesize that the co-administration of CD40L with antigen allows for CD4IND B-cell responses in vivo, and that mucosal boosting will enhance mucosal antigen-specific B-cell responses and confer protection against PCP.

Rationale: Preliminary studies demonstrated that CD40L co-administered with Kexin antigen results in CD4IND B-cell responses and protection against PCP. These studies will confirm these preliminary results.

Experimental Groups. The groups will be similar to those used in Example 19, but this study will assess responses to PC challenge. Male 6-8 week old BALB/c mice will be CD4-depleted by the administration of 0.3 mg GK1.5 IP by weekly injection, or given rat IgG as a control. 48 hours later, mice will be randomized to be vaccinated by 1M injection of pmini-Kexin WT, psec-mini-Kexin-WT, pmini-Kexin CO, or psec-mini-Kexin-CO, in each case either with or without CD40L. A control group of mice will be injected with pBudCD40L with no PC antigen. After 6 weeks mice will be further randomized, and either given no boosting or mucosal boosting with _$10^7$ adenovirus, encoding the same amount of antigen as the prime, again, with or without an equal dose of AdCD40L. At 9 weeks mice will be challenged with $2\times10^5$ PC cysts and followed for 6 weeks to determine PC lung burden by quantitative real time PCR. Sample Sizes will consist of 10 mice per group to give the power to resolve a 30% difference in PC burdens.

Manipulations: Plasmid injections will be repeated every after weeks for two doses as otherwise previously described by Ramsay et al. We will administer of E1-deleted Ad5 based vectors encoding antigen, with or without AdCD40L, by intranasal administration. Mice will be sacrificed 6 weeks after PC challenge to assay for serum and BAL anti-PC and anti-Kexin antibodies, PC burden by real time PCR, and GMS staining of lung tissue.

Measures and Outcomes: Sera will be assayed for anti-PC and anti-Kexin IgM, and IgG isotypes by ELISA at 3, 6, 9 and 15 weeks. Isotypes will be determined by using appropriate anti-mouse IgG isotypes: IgG1, IgG2a, IgG2b, IgG3 (Pierce, Rockford, Ill.). At sacrifice, one lung will be inflated with 10% neutral buffered formalin and sent for morphology examination using H & E and GMS staining. The other lung will be placed in TRIZOL®, a reagent for the isolation of high-quality total RNA, DNA, or protein, prior to assaying for PC burden by real time PCR. Serum and BAL antibodies will also be tested for complement-dependent killing, opsonic phagocytosis, and killing of PC in vitro as otherwise described above.

Expected Results and Interpretations; We expect to observe significant protection in mice vaccinated and boosted with adenovirus carrying DNA that encodes kexin antigens. Based on preliminary studies we expect to observe the greatest protection in the codon-optimized, secreted Kexin group. We expect to achieve a 6-log level of protection compared to CD40L vaccinated control mice without antigen. During the challenge studies we also will incorporate a scid mouse control group to verify infection with the dose of PC used, Both the scid group and the control, CD4-depleted mice typically have over $10^9$ PC copy number in their lung by week 6, Thus in the effective vaccine group we expect to observe levels of $10^3$ PC copy number or lower. We also expect to observe vaccine-induced increases in opsonic activity and killing of PC in vitro as well as protection in passive transfer experiments.

Alternative Approaches: The dosage of the boost will be optimized, The initial dose of $10^7$ has been validated in preliminary studies, but could be increased, e.g., to $10^8$ for both antigen-containing Ad, as well as for AdCD40L. We will also determine the duration of protection. We will choose the two most effective vaccine boost combinations (with and without CD40L), and challenge at week 16 or week 26 to determine whether protection still exists. We will also assess anti-PC and anti-Kexin recall responses in the lung and serum as well as B-cell Elipsots to assess functional B cell memory, Here we expect that CD40L will be required for long term functional B-cell responses. To confirm that the titer and half life of the antibody suffice to protect the scid mice, we will measure the titer immediately after transfer, and on day 28, Prior studies with DC-based vaccines suggest that 300 µl of serum should provide sufficient Ab to protect during the 28 day study period The relative importance of mucosal Ab and serum Ab to protective immunity can also be assayed, e.g., we could transfer concentrated BAL containing 100 µg of protein. Controls will consist of BAL that is brought up to 100 µg of protein with naive mouse serum, Example 21

Effect of mucosal boosting with recombinant MYA virus-based vectors after DNA priming in conferring protection against a PC challenge.

Hypothesis: We hypothesize that the co-administration of CD40L with antigen allows for CD4IND B-cell responses in vivo, and that mucosal boosting with modified vaccinia Ankara strain (MV A)-based vectors will enhance mucosal antigen specific B-cell responses and confer protection against PCP.

Rationale: Our preliminary studies have demonstrated that CD40L co-administered with Kexin antigen resulted in CD4IND B-cell responses and protection against PCP. However there could be a concern that an AdS-based vector might itself exacerbate HIV disease in patients with pre-existing AdS antibodies. Therefore, although our pre-clinical data support the efficacy of AdS-based vectors in rodents, it is possible that an alternative approach could be a useful option for at least some patients with HIV disease. We chose MVA vectors to explore such an alternative, as MVA elicits strong mucosal immune responses.

Experimental Groups. Male 6-8 week old BALB/c mice will be CD4-depleted by the administration of 0.3 mg GK1 0.5 IP by weekly injection, or given rat IgG as a control. 48 hours later mice will be randomized to be vaccinated by the IM injection of pmini-Kexin WT, psec-mini-Kexin-WT, pmini-Kexin CO, or psec-mini-Kexin-CO, in each case with or without CD40L. A control group of mice will be injected with pBudCD40L with no PC antigen. After 6 weeks mice will be further randomized, and given either no boost or mucosal boosting with ~$10^7$ MVA, encoding the same antigen construct as the prime, in each case either with or without an equal dose of MVA CD40L. A subgroup of mice will be sacrificed to determine pre-challenge antibody and B cell responses as outlined in Example 20, and the other mice will be challenged with $2\times10^5$ PC cysts and followed for 6 weeks. Sample sizes will consist of 10 mice per group to give the power to resolve a 30% difference in PC lung burden by quantitative real time PCR.

Manipulations: Plasmid injections will be repeated with a second dose after three weeks, as otherwise previously described by Ramsay et al. We will administer $10^7$ of MVA vectors encoding antigen, either with or without MVA CD40L, by intranasal administration. Mice will be sacrificed 6 weeks after PC challenge to determine serum and BAL anti-PC and anti-Kexin antibodies, PC burden by real time PCR, and GMS staining of lung tissue.

Measures and Outcomes: Sera will be assayed for anti-PC and anti-Kexin IgM, and IgG isotypes by ELISA at 3, 6, 9 and 15 weeks. Isotypes will be determined by using appropriate anti-mouse IgG isotypes: IgG1, IgG2a, IgG2b, IgG3 (Pierce, Rockford, Ill.). At sacrifice, one lung will be inflated with 10% neutral buffered formalin and sent for morphology examination using H & E and GMS staining. The other lung will be placed in TRIZOL®, a reagent for the isolation of high-quality total RNA, DNA, or protein, to assay PC burden by real time PCR.

Expected Results and Interpretations: We expect to observe significant protection in mice vaccinated and boosted with MVA vectors encoding kexin antigens. Based on our preliminary studies we expect the greatest protection will occur in the codon-optimized, secreted Kexin group. Our goal is to achieve a 6-log level of protection as compared to the control mice vaccinated with CD40L without antigen. During the challenge studies we also will incorporate a scid mouse control group to verify infection with the dose of PC used.

Alternative Approaches: The dosage of the boost will be optimized. The initial dose of $10^7$ has been validated in preliminary studies, but could be increased, e.g., to $10^8$ for both antigen and CD40L. If we observe significant protection, we will next determine the duration of protection. We will choose the two most effective vaccine boost combinations (with and without CD40L) and challenge at week 16 or week 26 to determine whether protection still exists. In these studies we will also assess anti-PC and anti-Kexin recall responses in lung and serum, as well as B-cell Elipsots to assess functional B cell memory. Here we expect that CD40L will be required for long term functional B-cell responses.

Example 22

Our hypothesis predicts that effective vaccination requires endogenous IL-23, and results in durable vaccine responses in both CD4+ T-cell deficient mice and CD40L knockout mice. We will examine the efficacy of CD40L co-transduction in CD40L knockout mice; and the requirement of IL-12 family members (including IL-12p35, IL-12p40, and IL-23), all critical activation molecules that are induced by CD40L-modified DCs in generating effective primary and memory B-cell responses. Our preliminary studies have suggested that IL-23 production is critical to generate B-cell memory against PC antigen.

Example 23

We investigate whether co-administration of CD40L with prime-boost vaccination can induce Ig class switching in CD40L knockout mice, and result in antigen-specific B-cell responses.

Hypothesis: We hypothesize that CD40L co-transduction with Kexin will result in class switching of B cells in CD40L KO mice and the generation of anti-Kexin IgG.

Rationale: Patients with mutations in CD40L resulting in Hyper-IgM syndrome are often infected by PC. There is an unfilled need for effective vaccines for these individuals.

Experimental Groups. Male PC-free 6-8 week old CD40L knockout or control mice will be randomized to be vaccinated by the 1M injection of pKexin based on the two most efficacious constructs identified above, followed by randomization for no boost, or boosting with AdKexin, or boosting with AdKexin1CD40L, or injection with AdCD40L alone as a control. Sample sizes will consist of 10 mice per group to give the resolution to detect a 30% difference in anti-Kexin or anti-PC IgG between different routes of vaccination. The optimal dose and route of the DNA prime and boost vector will be chosen based on the experimental results above.

Manipulations: Based on our preliminary studies we expect that plasmid injections will be repeated after three weeks for two doses, followed by a single boost with the viral vector three weeks later.

Measures and Outcomes: Sera will be assayed for anti-cPC/Kexin IgM, and IgG isotypes by ELISA at 3, 6, and 9 weeks. Isotypes will be determined by using appropriate anti-mouse IgG isotypes; IgG1, IgG2a, IgG2b, or IgG3 (Pierce, Rockford, Ill.). At 9 weeks, a subgroup will be boosted with an IN injection of $10^7$ particles of AdKexin (a recombinant adenovirus expressing Kexin). A control group will be left un-boosted, or boosted with AdCD40L. Three weeks after the boost, mice will be sacrificed and we will measure anti-PC/Kexin antibodies in serum and BAL fluid. Splenocytes and mediastinal lymph node cells will be harvested to determine the precursor frequency of antigen-specific B-cells by Elipsot. Serum antibodies will also be tested for complement-dependent killing, as well as opsonic phagocytosis and killing of PC in vitro as described above.

Expected Results and Interpretations: Based on our preliminary studies showing that AdCD40L delivery to the lungs resulted in a significant increase in anti-PC1 Kexin mucosal IgA and IgG, we expect that CD40L will most likely be optimal when included in both the prime and the boost. We also expect to observe an increase in opsonic killing of pC.

Alternative Approaches: If CD40L co-transduction in vivo is less effective than we expect, then we will perform co-culture experiments of irradiated AdCD40L (or control) modified DCs, pulsed with OVA to induce B cell proliferation and class switching in CD19+ B cells from CD40L KO mice. Particularly we will investigate the ratio of DC's to B cells to induce differentiation and generation of anti-OVA IgG in vitro. If higher ratios of DCs are required to induce B cell proliferation in CD40L KO mice as compared to control C57BL16 mice, then we will investigate the effects of higher doses of DNA priming, boosting, or both in vivo.

Secondly, if we observe a significant amount of class switched antibody against PC in CD40L KO mice, we will repeat the experiment with a PC challenge as outlined above, to examine the efficacy and duration of protection in these mice. If we observe efficacy with the MV A platform, we will also repeat this experiment substituting MV A vectors for Ad vectors to examine their efficacy and duration of protection.

Example 24

Examine the role of IL-12p35, IL-12p40. and 11-23 in mucosal prime boosting with recombinant adenovirus virus-based vectors against PC.

Hypothesis: We hypothesize that the co-administration of CD40L with antigen allows for CD4IND B-ceJ1 responses in vivo, and that mucosal boosting will enhance mucosal antigen specific B-cell responses and enhance protection against PCP.

Rationale: Our preliminary studies demonstrated that CD40L-modified DCs required IL-23 for a functional B-cell recall response to PC antigen when the DCs were pulsed with PC organisms. However, these preliminary results do not in themselves show whether IL-23 is also required for the prime boost regimen in vivo. If IL-23 is indeed required in vivo, then IL-23 could be used as a mucosal adjuvant. Secondly, up to 3-7% of the population is heterozygous for a non-synonymous SNP in the IL-23R coding region. It is possible that this polymorphism could reduce the immunogenicity of the novel vaccine platform in heterozygous individuals, or in individuals homozygous for the less frequent allele.

Experimental Groups. Male 6-8 week old BALB/c mIce will be CD4-depleted by the administration of 0.3 mg GrO.5 IP by weekly injection. 48 hours later, mice will be randomized to be vaccinated by the 1M injection of the two most efficacious Kexin constructs as identified above: pmini-Kexin WT, psec-mini-Kexin-WT, pmini-Kexin CO, or psec-mini-Kexin-CO with CD40L. Control mice will be injected with pBudCD40L with no PC antigen. After 6 weeks the mice will be further randomized to no boost or mucosal boosting with $10^7$ adenovirus encoding the same antigen construct as the prime, in each case with or without an equal dose of AdCD40L or $10^7$ of fowl pox vectors encoding the same antigen (with our without CD40L). Either an adenovirus vector or an MVA vector will be used, based on their relative efficacy as determined in the experiments described above. At 9 weeks 50% of the mice will be sacrificed to examine serum and mucosal anti-Kexin1PC antibodies as well as antigen-specific B-cells. The other 50% will be challenged with $2 \times 10^5$ PC cysts intratracheally and sacrificed 7 days later tc assess the role of IL-23 in regulating antigen specific B-cell recall responses. Sample sizes will consist of 10 mice per group to give the statistical resolution to detect a 30% difference in antigen specific B-ceJ1 responses.

Measures and Outcomes: At the time of sacrifice (either week 9 or week 10 in PC challenged mice) lungs will be lavaged for anti-PC and anti-Kexin IgA levels. Kexin-specific, IgG-expressing B cells in the spleen and mediastinal lymph nodes will be assayed by Elispot. One lung will be placed in TRIZOL®, a reagent for the isolation of high-quality total RNA, DNA, or protein, for measuring PC mtLSU copy number by real time PCR. Serum antibodies will be tested for complement-dependent killing, as well as opsonic phagocytosis and killing of PC in vitro as described above.

Expected Results. Interpretations and Alternative Approaches: We expect to observe the induction of anti-PC and anti-Kexin primal)' antibody responses in the serum of all mice. However, we expect to observe a defect in mucosal boost responses as well as PC recall response in the lungs of IL-23- and IL-12p40-deficient mice. We also expect to observe an increase in opsonic killing of PC in IL-23 intact mice (only). Such results would be consistent with the expected role of IL-23 in expanding the B-cell memory pool. If this is indeed the case, then we will repeat the experiment and examine the effect of adding AdIL-23 (or MVA IL-23) in the boost along with AdCD40L to determine whether exogenous IL-23 can restore B-cell expansion in IL-12p40-1- or IL-23p19-1-mice. We have previously prepared the AdIL-23 vector. Preliminary studies suggest that the AdIL-23 vector will restore B-cell memory responses, at least in the context of ex vivo, pulsed DC-based vaccination with IL-23p 19-/-DCs.

Example 25

Testing in vivo. CD4IND, pathogen-specific immune responses against *Pneumocystis* kexin are generated in an SIV model of immunodeficiency in macaques. We will confirm that the mini-kexin constructs produce vaccine-induced immune responses in SIV-infected, CD4-deficient macaques. Control or SIV-infected macaques will undergo DNA priming followed by mucosal boosting 4 weeks after mock or Jive SIV infection. Outcome measures will include humoral responses to the vaccine and the prevention of *Pneumocystis* colonization as determined by PCR in BAL fluid.

Example 26

Evaluate the effect of CD40L on monkey DCs.

Hypothesis: We hypothesize that AdhCD40L-transduced (or MV A hCD40L transduced) monkey DC's will demonstrate maturation by an increase in Class II MHC expression, and that they will demonstrate activation by enhanced elaboration of IL-12 and IL-23 in culture.

Rationale: Preliminary studies have demonstrated similar results m the mouse model. We therefore expect similar results in the macaques.

Experimental Groups. Monkey DC's from juvenile macaques with normal CD4 counts will be purified by CD 11 c+ beads (Mitenyi Biotech) from peripheral blood.

Monkey DC's will be grown in RPMI 1640 and then mock transfected with PBS; or transfected with AdEGFP or with AdhCD40L at MOIs of 5, 10, 50, and 100. We will carry out similar experiments with MY A CD40L. Sample sizes will consist of 4-6 control macaques; and transductions will be carried out in triplicate.

Manipulations: CD11c+ DCs will be cultured in RPMI 1640 growth medium supplemented with 1% monkey plasma. 50,000 to 100,000 cells will be analyzed by four-color FACS for each of the following DC markers: anti-HLA-DR, CDSO, CD86, and CD25 from B-D Pharmingen, and CD83 from Coulter. Immature DC's are typically HLA-$DR^{++}$, $CD86^{++}$, $CD80^{+/low}$, $CD83^{-/weak}$ and CD25−, whereas mature DC's are HLA-$DR^{+++}$ $CD86^{+++}$, $CD25^{++}$, $CD80^{++}$, and $CD83^{++}$. The remaining DC's will be transduced with MOIs of 0, 5, 10, 50, or 100 of AdEGFP or AdhCD40L (or MVA vectors) and cultured for 24 hours. The supernatant will be harvested for determinations of monkey IL-12 (p40 and p70) and TNF-alpha (Biosource, Camarillo, Calif.). The cells will be stained for maturation markers as outlined above, as well as for CD40L with clone TRAP-1-PE from Immunotech (Westbrook Me.). IL-23 will be measured by ELISA (Bender MedSystems).

Expected Results and Interpretations: We expect to observe dose-dependent transduction of Monkey DC's by both AdEGFP and AdhCD40L, as measured by an increase in the mean channel fluorescence of GFP in AdEGFP-transduced cells, and by an increase in CD40L as measured by TRAP-1 PE staining. Bioactivity of AdhCD40L will be assessed by the ability of the vector to selectively induce IL-12, IL-23, and TNF-alpha in supernatants from AdhCD40L-transduced DCs. We also expect to observe the maturation of DC's transduced with AdhCD40L as measured by an increase in mean channel fluorescence in HLA-DR., CD86, and CD83 expression. There may also be some increase in HLA-DR, CD86, and CD83 expression in AdEGFP-transduced cells.

Alternative Approaches: We expect efficient transduction of DCs with an MOI of 100. Moreover, human CD40L (h CD40L) has 99% homology with CD40L from monkey. Preliminary studies show that hCD40L induces IL-12p70 in monkey DCs. Thus we expect that hCD40L should have bioactivity in this system. If, however, we observe a defect in DC activation, we will assess hCD40L at the protein level by FASC and at the transcript level by RT-PCR to verify its expression in DCs with the Ad vector or the MVA vector.

Example 27

Generating Kex1 antigen-specific IgG in SIV-infected macaques by heterologous, prime-boost immunizations.

Hypothesis: We hypothesize that DNA priming followed by heterologous adenovirus or MVA virus boosting will elicit potent anti-Kex1 systemic and mucosal antibody responses and protection against PC colonization.

Rationale: The results of the prior studies will help us choose which Kexin DNA construct to use in macaques, and whether to use adenovirus or MVA as the boost.

Experimental Groups. There will be five vaccine groups:
1. SIV-uninfected, *pneumocystis* vaccine with CD40L (n=8)
2. SIV-infected, *pneumocystis* vaccine with CD40L (n=8)
3. SIV-uninfected, *pneumocystis* vaccine without CD40L (n=4)
4. SIV-infected, sham vaccine, without PC challenge (n=3)
5. SIV-uninfected, sham vaccine, without PC challenge (n=3)

Due to expense and the likelihood that the *pneumocystis* vaccine alone (without CD40L) will not elicit strong humoral immunity, the SIV-uninfected, *pneumocystis* vaccine without CD40L group (Group 3) may be omitted from the study.

Groups 4 and 5 will be used as shared controls.

Manipulations, Measurements, and Outcomes: Animals (male juvenile Rhesus macaques) will be pre-screened by ELISA for anti-PC Kexin titers and anti-adenovirus titers (the latter, if we choose an adenovirus platfonn). Only animals with negligible titers, defined as less than 1:64 (OD450 cutoff of 0.1), will be enrolled. At −4 weeks monkeys will be infected with SIVmac251, or mock infected with saline injection.

The dose of virus will be 50 TC1D50. Inoculations will be made intravenously, via the saphenous vein. At week 0, the macaques will undergo a baseline bronchoscopy, they will be assessed for serum and BAL anti-Kex I antibodies, and they will be assessed for PC colonization by nested and real time PCR. BAL fluid will be obtained by bronchoscopy in anesthetized animals. Plasmid DNA will be administered at a dose of 2 mg 1M (2 sites [quadriceps], at 1 mg each in 0.5 ml saline). The plasmid DNA will encode the Kex1 construct that has shown the greatest efficacy in mice, with or without CD40L, as appropriate for each of the group assignments listed above. DNA will be administered at weeks 0 and 3 (i.e., 4 and 7 weeks after mock or live SIV infection). At week 6 monkeys will undergo another bronchoscopy, and blood samples will be taken to determine pre-boost anti-Kex1 antibodies in serum and BAL. Following the bronchoscopy, a boost immunization will be administered intranasally with adenovirus (1010 pfu) or MVA ($10^8$) encoding Kex1 and hCDC40L, or encoding Kex1 alone for monkeys in the no-CD40L group. A third bronchoscopy will be performed at week 8 to assess the effect of the boost on anti-Kex1 IgG in serum, and anti-Kex1 19A in BAL. Two more bronchoscopies will be performed at weeks 20 and 32 to assess longevity of the antibody responses, as well as the level of *Pneumocystis* colonization as determined by both nested and real time PCR. At week 32 we will harvest mediastinal lymph nodes for B-cell Elispot assays, and lung tissue for histology.

Real-time PCR will also be used to assess PC colonization in the lungs. To monitor the safety of the approach in the macaque model we will also obtain complete blood counts and serum chemistries, including liver transaminases, at weeks 6, 8, 20, and 32.

Expected Results and Interpretations: We expect that the Kex1/CD40L vaccination procedure will be safe and will not have associated hematological or liver toxicity. We expect to observe significant increases in antigen-specific IgG in both SIV+ and SIV animals receiving hCD40L with Kex1. Moreover, we expect higher anti-Kex1 IgG and 19A levels in SIV-animals receiving the Kex1/CD40L combination as compared to Kex1 alone. Moreover we expect the addition of a mucosal boost will significantly augment the levels of anti-Kex1 IgG and IgA in BAL fluid (particularly in the Kex11CD40L groups). We expect to observe that the Kex11CD40L vaccine will be associated with reduced PC colonization in the BAL at week 20, and in the BAL and lung tissue at week 32 in SIV-infected monkeys as compared to the group 4 or 5 animals.

Alternative Approaches: If we observe significant increases in anti-Kex1 IgG in SIV-animals but not in SIV+ animals, such an outcome could be due to inadequate DC homing or an inadequate dose of the boost. If that should be the case, then we will repeat a mucosal boost with one log higher virus dose. Our primary measurement in these experiments will be the level of PC colonization, as determined by nested and real time PCR. In humans these two assays have over a 93% concordance rate. To assess, 25 SIV-positive and 25 SW-negative lung tissue samples and paired BAL samples will be tested to determine the prevalence of PC colonization at necropsy in these monkeys. Assuming the figure is at least 60% for the srv-positive cohort, then this set of experiments should provide a meaningful outcome. If the figure should be lower, then we will identify lung samples with high burdens of CP organisms, and isolate organisms from those samples to use for inoculation at week 20. Lungs from identified animals will be disrupted and processed as has been previously described for murine lung; cysts will be purified by sucrose gradient purification.

Example 28

*Pneumocystis* is also a common infection following medically-induced immunosuppression, for example in cancer chemotherapy, or in suppressing host rejection of transplanted tissues or organs. Vaccination with mini-kexin can protect against PCP in such instances.

As a demonstration in a mouse model, we performed DNA plasmid mini-Kexin prime-boost vaccination in wild type mice, and then depleted CD4+ T-cells. Depletion of CD4+ T-cells makes unvaccinated mice susceptible to PCP. Female 6- to 8-week-old C57BL16 and BALB/c wild type (wt) mice were immunized intramuscularly with a mini Kexin-encoded, pBUD plasmid vector twice, two-weeks apart. The four mini Kexin vectors encoded secreted (s) or non-secreted versions of mini kexin, either codon-optimized (co) or wild type (wt). Two weeks after the second plasmid DNA prime vaccination, the mice were intranasally boosted with recombinant adenovirus encoding the same type of mini-Kexin as had been used in the prime vaccination. Because the vaccinated mice initially had normal levels of CD4+ T-cells, we did not include CD40L in either the priming or boosting vector. To artificially induce an immunosuppressed state, the mice were then depleted of CD4+ T cells by administration of monoclonal antibody GK1.5, repeated weekly, starting two weeks after the boost. After one week of CD4+ depletion, the mice were challenged intratracheally with $2\times10^5$ PC organisms per mouse. Four weeks later the mice were euthanized, and lung tissues were collected for PC organism burden (assayed by real-time PCR).

Figure 5:
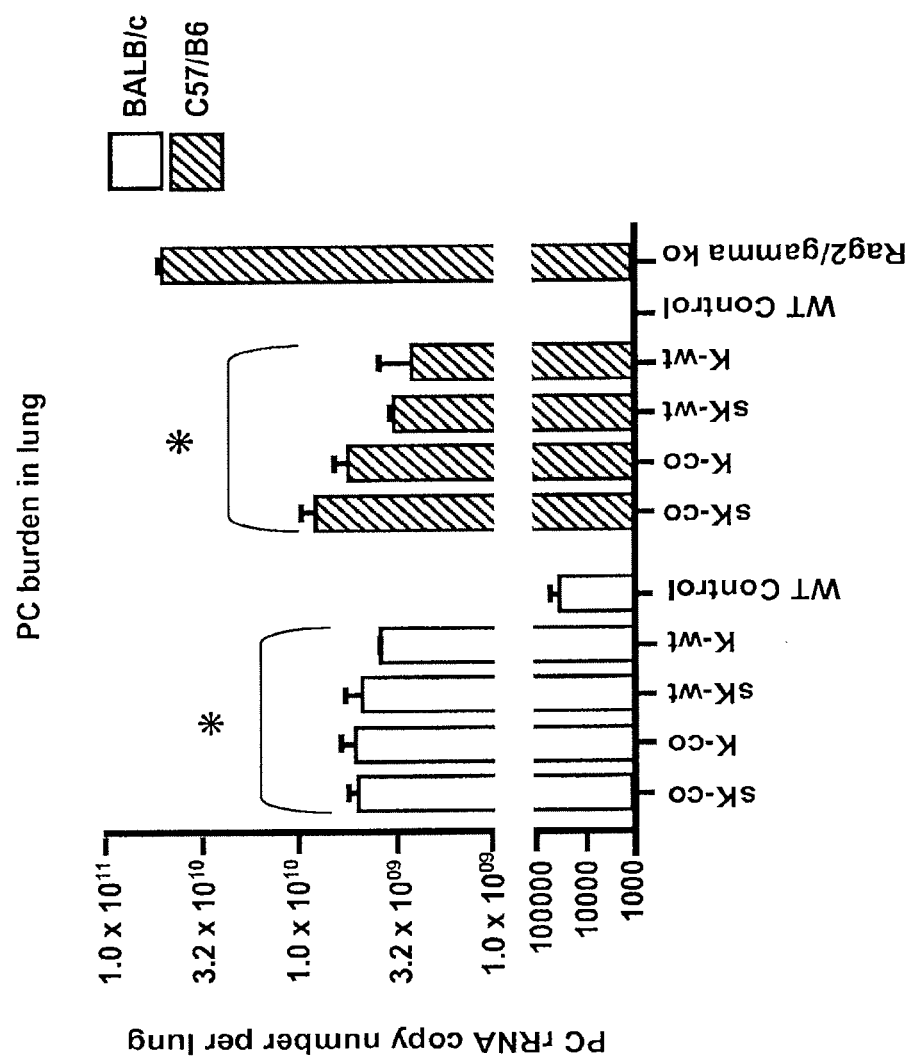
FIG. 5 depicts the results of PC challenge in prime-boost vaccinated mice that were artificially immunosuppressed.

As shown m FIG. 5, all four miniKexin plasmid vaccines provided significant protection against PC infection, as compared to Rag2/gamma chain double-knockout mice, which lack B, T, and NK cells (n=5-6 per group, *denotes P<0.05, Student's-t-test as compared to RAG2/gamma C KO).

Example 29

Following successful completion of animal trials, vaccines in accordance with the present invention are tested in human patients in clinical trials conducted in compliance with applicable laws and regulations.

Example 30

Detailed Methodology. Except as otherwise stated, the following materials and procedures have been used or will be used in the experiments described above:

1. Animals. Virus-free BALB/c mice, aged 6-8 weeks, will be purchased from NCII Charles River. Preliminary experiments have shown that animals from this supplier are not chronically infected with P. carinii. IL-12p35, IL-12p40, and IL-23p19 mice on a C57BL16 background are maintained in our laboratory. Homozygous C.B 17 scidlscid (scid) mice will be purchased from NCI/Charles River or Taconic Laboratories in Germantown, N.Y. All animals will be housed in separate rooms at the LSD Medical Center Animal Care Facility in HEPA-filtered ventilated racks. Mice are fed autoclaved chow and water ad libitum, and are held in the facility for least 2 days before initiating treatment. Changes of animal cages, bedding, water bottles, and food will be performed in a laminar flow hood. Access to the room is limited to specific laboratory personnel and animal care personnel; gown and gloves are required for all workers entering the room. It is estimated that we will use a total of 1368 mice in the experiments described. Macaques are housed at the Tulane National Primate Research Center. Where applicable, monkeys are pre-anesthetized with acepromazine (0.2 mg/kg, i.m.) and sedated with ketamine-HCl (10 mg/kg, i.m.) for bronchoscopy and blood sampling. Bronchoscopy will be performed with topical anesthesia with 2% xylocaine.

2. Monitoring Animal Health. Sentinel DBA mice are co-housed in the same room as the experimental mice, with bedding regularly taken from the cages of P. carinii-infected and scid mice. The sentinel mice are sacrificed quarterly and tested for antibody titers to a variety of murine viruses and pathogens. Regular consultation with veterinary staff is used to assure and to confirm specific-pathogen-free conditions for the experimental animals.

3. Maintenance of P. carinii in scid or CD40L knockout mice. To assure a consistent supply of P. carinii, the P. carinii organisms will be passaged through the lungs of C.B17 scidlscid (on a BALB/c background) or CD40L KO mice (on a C57BL16 background). We presently maintain a breeding colony of PC-free and PC-infected CD40L KO mice in separate rooms. Groups of scid or CD40L KO mice will be inoculated with P. carinii organisms as described below. Inoculated mice will be housed in ventilated racks for 4-6 weeks before being sacrificed to harvest P. carinii from lung tissue.

4. Inoculation of Mice with P. carinii organisms. P. carinii organisms used for inoculation will be prepared from homogenized lungs of chronically infected scid or CD40L KO mice. We have previously used athymic mice, but have found that scid mice develop more consistent and intense infections. The C.B17 scid mouse strain is allotype co-isogenic to BALB/c mice. Briefly, lung tissue will be obtained from scid or CD40L KO mice chronically infected with P. carinii. The lungs will be frozen for 30 minutes, and then disrupted mechanically in a small tissue processor, a STOMACHER® 80 BIOMASTER. The disrupted lung tissue will be filtered through gauze and adjusted to a level of $2\times10^6$ cysts/ml, as assessed by a histological staining technique, DIFF-QUICK® Romanowski staining. P. carinii will then be injected into the trachea-of lightly anesthetized BALB/c mice by passing a blunt needle into the trachea per os and then threading a catheter through the needle into the low trachea. Each mouse will receive 0.1 ml of inoculum ($2\times10^5$ cysts), followed by 0.8 ml of air. To assure viability of the organisms, the inoculum will be injected into recipient mice on the day of preparation. Lung homogenates containing P. carinii will be routinely checked for endotoxin contamination using the Whitaker endotoxin assay. The inoculum will also be quantified using a gene expression analysis, TAQMAN®-based assay for rRNA copy number. For antigen preparation, PC organisms will be isolated from lung tissue of C.B-17 scid mice (for experiments in BALB/c mice) or CD40L KO mice (for experiments in C57BL16 mice) that were previously inoculated with PC. PC organisms will be purified by differential centrifugation, and protein antigen will be produced by sonication for 5 minutes.

5. Examination of Lung Tissue for P. carinii Infection. Lung tissue will be fixed in formalin and stained with Gomori's methenamine silver and hematoxylin and eosin stain.

6. Controls for Bacterial/Fungal/Viral Infection. Random samples of lung tissue from control and experimental mice will be cultured to exclude the possibility of intercurrent bacterial or fungal infection. In addition, when the experimental design permits, touch preps will be made of lung tissue prior to formalin fixation and gram staining to look for bacterial infection. Also, co-housed sentinel DBA mice are routinely monitored for serologic titers against common viral pathogens, including Sendai and Mouse Hepatitis Virus.

7. Depletion of host CD4+ lymphocytes. The hybridoma GK1.5 (rat antiCD4) was originally obtained from the American Type Culture Collection (Manassas, Va.) and is maintained in the LSU Monoclonal Antibody Facility. GK1.5 is a rat IgG2b monoclonal antibody. Antibodies from this hybridoma are prepared from ascites in athymic mice. The antibodies are partially purified by ammonium sulfate precipitation, dialyzed against phosphate buffered saline, and quantified by protein electrophoresis and optical density. To deplete mice of CD4+ T lymphocytes, mice will receive an intraperitoneal injection of 0.3 mg anti-CD4 monoclonal antibody in 0.2 ml PBS. Control mice will receive an equal volume of rat IgG. Depletion of CD4+ lymphocytes will be checked by flow cytometric analysis of splenocytes or peripheral blood as described below. Depletion of the appropriate lymphocyte subset will be maintained by weekly administration of the antibodies for the course of the experiment.

8. RNA isolation and gene expression analysis, TAQMAN® probes and primers for PC rRNA. Total RNA is isolated from the right lung of infected mice by a single step method using TRIZOL®, a reagent for the isolation of high-quality RNA, DNA, or protein (Life Technologies, CA, USA). As a standard for the assay, a portion of PC muris rRNA (GenBank Accession No. AF257179) is cloned into PCR2.1 (Invitrogen, Carlsbad, Calif.), and PC rRNA is produced by in vitro transcription using T7 RNA polymerase. The template is digested with RNase-free DNase, quantified by spectrophotometry and aliquoted at −80° C. until used. The gene expression analysis TAQMAN® PCR primers for mouse PC rRNA are 5'-ATG AGG TGA AAA GTC GAA AGG G-3' (SEQ ID NO. 2) and 5'-TGA ITG TCT CAG ATG AAA AAC CTC IT-3' (SEQ ID NO. 3). The probe is labeled with a fluorescent reporter dye, 6-carboxyfluorescein (FAM), and the sequence is 6FAM-ACAGCCCA-GAATAATGAATAAAGITCCTCAAITGTTAC-TAMRA (SEQ ID NO. 4). (TAMRA=tetramethyl-6-Carboxyrhodamine.) Real-time PCR is carried out using one-step gene expression analysis, TAQMAN® RT-PCR reagents (Applied Biosystems, Foster City, Calif.). The PCR amplification is performed for 40 cycles: 94° C. for 20 s and 60° C. for 1 min, in triplicate using the ABI Prism 7700 SDS. The threshold cycle CT values are averaged from the values obtained from each reaction, and data are converted to rRNA copy number using a standard curve. This assay has a correlation coefficient greater than 0.98 over 8-logs of PC RNA concentration, and is known to correlate with viable PC since either heat killing or exposure to trimethoprim-sulfamethoxazole ablates the signal.

9. *Pneumocystis* viability assay. Macrophages ($10^6$/ml) suspended in a volume of 100 µl of RPMI 1640 medium containing FCS are co-cultured in round-bottom 96-well plates with PC ($2\times10^4$ cysts/ml, 50 µl), yielding an effector-to-total-PC organism ratio of 1:1 (estimated 1:10 cyst to trophozoite ratio). Before addition of PC, organisms will be preopsonized with 50 µl of serially diluted serum or normalized BAL, or 50 µl of DMEM plus 10% FCS. Included as a viability control are PC organisms incubated with control medium, DMEM plus 10% FCS. The plates are spun at 2500 rpm to pellet the PC organisms. The supernatants and cell pellets are collected, and total RNA is isolated using TRIZOL® LS, a reagent for the isolation of high-quality total RNA, DNA, or protein, (Invitrogen Life Technologies). Viability of the PC is analyzed with real-time PCR measurement of PC large subunit rRNA copy number (GenBank accession number AF257179), and quantified against a standard curve. This method detects viable PC organisms, as evidenced by loss of detectable PC rRNA in heat-killed organisms or those exposed to trimethoprim/sulfamethoxazole.

10. PC Kex 1 ELISA. To determine anti-PC or Kex1 IgG titers, ELISA plates (Corning, N.Y.) are coated with 100 ng of PC antigen or Kex 1 antigen per well in carbonate buffer at pH 9.5, and held overnight. Plates are washed with PBS+0.05% polysorbate 20 detergent, TWEEN®-20 (wash buffer) and blocked with bovine serum albumin and 2% milk. After washing, serial dilutions of serum will be added to each well and incubated for one hour at room temperature. Then, after washing, 100 µl of 1:1000 alkaline phosphatase conjugated goat anti-mouse IgG or IgA (Bio-RAD, Hercules, Calif.) will be added and incubated for one hour at room temperature. Then, after washing, the plates are developed using Sigma 104 substrate tablets in diethanolamine buffer, and absorbance is measured at 490 nm. Anti-PC and anti-Kex1 specific mouse IgG isotypes will be assayed. For macaque antibodies we use anti-Rhesus IgA and IgG.

11. Bronchoalveolar lavage. Lavaged lymphocytes will be obtained by bronchoalveolar lavage of mice anesthetized with intraperitoneal pentobarbital. This technique has been previously used in our laboratory to recover lung cells from mice, rats, and monkeys. For mouse studies, the lungs will be lavaged through an intratracheal catheter with warm (37° C.) calcium- and magnesium-deficient PBS supplemented with 0.5 mM EDTA. A total of 11 ml will be used for each mouse in 0.5 ml increments, with a 30 second dwell time. This technique recovers $0.5-1\times10^6$ cells from normal animals, of which greater than 95% are alveolar macrophages, with greater than 95% viability as measured by trypan blue exclusion. In mice inoculated with *P. carinii*, total cell count can be as high as $4-6\times10^6$, and the percentage of lymphocytes contained within the lavaged cells is as high as 50%. For some studies, the first 1.0 ml of BAL fluid may be frozen for cytokine analysis, or BAL fluid may be concentrated to recover detectable cytokine or IgA.

12. Retrieval of hilar and paratracheal lymph nodes. Hilar lymph nodes and paratracheal (mediastinal) lymph nodes will be resected under sterile conditions from mice given a lethal dose of pentobarbital. This method has been used to study draining lymph node cells from mice challenged with antigen. The lymph nodes will be passed through a sterile mesh screen into culture medium, and adjusted for cell number with a hemocytometer. Using this technique, approximately $12-15\times10^6$ cells are recovered from a mouse inoculated with *P. carinii*. More than 90% of these cells are lymphocytes as measured by a histological staining technique, DIFF-QUICK® staining. Cells will be processed for flow cytometry as outlined above.

13. B-cell Elipsots. To determine precursor frequency of Kex1 specific IgG B-cells, we will perform ELISPOT assays using FACS-sorted B cell populations. 96-well PVDF filter plates will be coated with Kex1, and serial dilutions of sorted B cells will be applied to the wells. Anti-Kex1 antibodies captured on the filter will be visualized by staining with an AP-conjugated anti-IgG or IgA secondary antibody. After developing with chromogenic substrate, the plates will be counted using an automated plate reader, and the percentage of antibody producing cells in each subset will be calculated.

14. DNA Vaccination. For intramuscular delivery, mice are anesthetized with isoflurane. Then 100 microgram of the DNA vaccine is delivered in 100 III of normal saline to the tibialis muscle (i.e., 50 III per hind leg) using a fine-needle (30G) tuberculin syringe. If needed, we will follow immediately by mild electroporation using a BIX ECM 830 electroporator apparatus with caliper electrodes (Harvard Biosciences). Immediately following injection of DNA to each leg, the calipers will be set to 4-5 mm and placed tightly on either side of the tibialis. The machine will be discharged mice, resulting in 2×20 millisecond pulses of 150V at an interval of 1 sec.

15. Statistical Analysis. Data will be analyzed using StatView statistical software (Brainpower Inc., Calabasas, Calif. Comparisons between groups will be made with the Student's t-test, and comparisons among multiple groups will be made with analyses of variance and appropriate follow-up testing. The Mann-Whitney test or the Wilcoxson paired sample test will make ordinal comparisons. Significance will be taken as $p<0.05$.

Example 31

Use and Care of Vertebrate Animals

1. Justification for the Use of Experimental Animals: There are no alternatives to the use of live animals to study host defense mechanisms, nor to study vaccine responses against *Pneumocystis*. *Pneumocystis* cannot be reliably maintained in vitro, so research with this pathogen requires the use of animal models of infection. Rhesus monkeys are being used because of the similarities between infection of this species with simian immunodeficiency virus (SIV) and human infection with HIV/AIDS.

2. Veterinary Care of Experimental Animals: Mice will be housed in a separate room at the LSD Medical Center Animal Care Facility in ventilated rack caging. This facility is State-licensed and fully accredited by the American Association for Accreditation of Laboratory Animal Care (AAALAC). Animals are housed under specific-pathogen-free conditions. Personnel access to the animal room is limited. All food, cages, water, and bedding is autoclaved prior to use. Gowns, gloves, and mask are required to handle the animals. All cage, food, and bedding changes take place in a laminar flow biosafety hood in the same room. Sentinel animals are housed in the same room with sample bedding from the immunosuppressed animals. Serum from these sentinel animals is routinely screened for a battery of murine pathogens. A veterinarian oversees the facility.

Veterinary care of the macaques at the Tulane National Primate Research Center will be handled similarly. The animals undergoing study will be monitored closely for food and water intake, and routine blood work will be limited to 40 cc/month. The primate center has strict protocols in place to euthanize SIV-infected animals when weight loss or other clinical parameters indicate significant morbidity. Animals to be infected with SIV will receive 50 TCID50 of strain S1Vmac251, a pathogenic strain to which animals have had a median survival of 210 days in past studies. Basic monitoring will include: 1) twice daily observations by a trained animal care technician, 2) physical examinations including blood sampling prior to SIV inoculation, after SIV inoculation, and at bi-monthly intervals thereafter. All physical examinations and invasive procedures will be performed on anesthetized animals. The anesthetic used will either be a combination of ketamine-HCl (10 mg/kg, i.m.) and acepromazine (0.2 mg/kg, i.m.), or a dissociative anesthetic classified as an NMDA receptor antagonist, TELAZOL® (5 mg/kg of Tiletamine and Zolazepam).

Containment practices at the Tulane Primate Center are in accordance with the recommended guidelines in the Center for Disease Control Morbidity and Mortality Weekly Report, vol. 31 (#43) "AIDS: Precautions for Clinical and Laboratory Staff, pp. 577-580 (1982); vol. 32 (#34) "AIDS: Precautions for Health Care Workers and Applied Professionals" pp. 577-580 (1983); and the Biosafety in Microbiological and Biomedical Laboratories Guidelines, First edition (1984).

3. Experimental Procedures involving Live Animals:

a. Intratracheal Inoculation with *P. carinii* Organisms: *Pneumocystis carinii* organisms will be obtained from the lungs of chronically infected scid or CD40L KO mice. Organisms for this colony of infected mice were originally obtained from the Fox Chase Cancer Center in Philadelphia, PA. Mice will be sacrificed by a lethal (400 mglkg) dose of IP pentobarbital, followed by exsanguination once they are deeply asleep. The lungs will then be removed aseptically, and *Pneumocystis carinii* organisms will be recovered for injection into other scid mice (to maintain the organisms) or into BALBC mice (to conduct the proposed experiments). The *Pneumocystis carinii* organisms will be injected in a volume of 0.1 ml into the tracheas of mice lightly anesthetized with inhaled isoflurane. Once the animals are asleep, the animals are briefly suspended by their teeth, the tongue is gently pulled forward with tweezers, and the inoculum is injected into the lungs using a blunt 18 g needle. These inoculations do not appear to cause undue discomfort or pain, and are (themselves) associated with minimal mortality. Once the injected animals have recovered from the anesthesia, they (initially) appear healthy.

Mice will not receive analgesics after intratracheal inoculations for the following reasons: a) Many analgesics are known to alter the host response to infection and endotoxin. b) There is no evidence that mice undergoing this procedure experience pain or discomfort. c) Most analgesics have an extremely short half life in rodents, which would necessitate multiple injections, that could become a stress in themselves.

b. Depletion of CD4+ lymphocytes: Mice will be depleted of lymphocytes by weekly intraperitoneal injections (0.2 ml) with an anti-CD4 monoclonal antibody. This procedure effectively depletes treated animals of targeted T lymphocytes in blood and lymphoid tissue with minimal morbidity and no mortality (in itself). Treated animals do not lose weight and they (initially) appear healthy.

c. DNA vaccination and mucosal boosting: Mice will be injected under isoflurane anesthesia with endotoxin-free plasmid DNA, 100 pg, split in two injections, one into each tibialis anterior muscle. Mucosal boosting is performed by the intranasal administration of virus under isoflurane anesthesia.

Example 32

Uses Against Other Pathogenic Fungi

The methods and constructs of this invention are also expected to be effective in conferring immunity against at least some other pathogenic fungi, for example, *Candida glabrata* and *Candida albicans*, both of which are human pathogens. A sequence alignment program (BLAST®) comparison of the kexin amino acid sequences in these two species versus that of *P. carinii* showed 53% homology with that of *C. glabrata* and 50% with that of *C. albicans*. Effectiveness against other fungal species with −40% or more amino acid sequence homology is expected.

REFERENCES

1. L Zheng, M" Ramsay, A J., Robichaux, M. B., Norris, K. A., Kliment, C., Crowe, C., Rapaka, R. R., Steele, C., 1. McAllister, F., Shellito, J. E. et al 2005. CD4 T cell-independent DNA vaccination against opportunistic infections. J Clin Invest.
2. Murray, J. F., Felton, C. P., Garay, S. M., Gottlieb, M. S., Hopewell, P C, Stover, D. E., and Teirstein, A. S. 1984. Pulmonary complications of the acquired immunodeficiency syndrome. Report of a National Heart, Lung, and Blood Institute workshop. N Engl. J. Med. 310:1682-1688.
3. Ives, N. J., Gazzard, B. G., and Easterbrook, P. J. 2001. The changing pattern of aids-defining illnesses with the introduction of highly active antiretroviral therapy (haart) in a london clinic. J Inject. 42:134-139.
4. Hoover, D. R., Saah, A. J., Bacellar, H., Phair, J., Detels, R., Anderson, R., and Kaslow, R. A. 1993. Clinical manifestations of AIDS in the era of *pneumocystis* prophylaxis. Multicenter AIDS Cohort Study. N Engl. J Med 329:1922-1926.
5. Bozzette, S. A., Finkelstein, D. M., Spector, S. A., Frame, P., Powderly, W. G., He, W., Phillips, L., Craven, D., van, d. H., and Feinberg,]. 1995. A randomized trial of three antipneumocystis agents in patients with advanced human immunodeficiency virus infection. NIAID AIDS Clinical Trials Group. N. Engl. J. Med 332:693-699.
6. Wallace, J. M., Hansen, N. I., Lavange, L., Glassroth, J., Browdy, B L, Rosen, M. J., Kvale, P. A., Mangura, B. T., Reichman, L. B. et al 1997. Respiratory disease trends in the Pulmonary Complications of HIV Infection Study cohort. Pulmonary Complications of HIV Infection Study Group. American Journal of Respiratory & Critical Care Medicine 155:72-80.
7. Simonds, R. J., Hughes, W. T., Feinberg'].., and Navin, T. R. 1995. Preventing *Pneumocystis carinii* pneumonia in persons infected with human immunodeficiency virus. [Review] [41 refs]. Clinical InfectiOUS Diseases 21 Suppll:S44-S48.
8. Ledergerber, B., Mocroft, A., Reiss, P., Furrer, H., Kirk, O., Bickel, M., Uberti-Foppa, C., Pradier, C., d'Arminio, M. A., Schneider, M. M. et al 2001. Discontinuation of secondary prophylaxis against *Pneumocystis carinii* pneumonia in patients with H1V infection who have a response to antiretroviral therapy. Eight European Study Groups. N. Engl. J Med 344:168-174.
9. Lopez Bemaldo de Quiros J C, Miro, J. M., Pena, J. M., Poclzamczer, D., Alberdi, J. C., Martinez, E., Cosin, J., Claramonte, X., Gonzalez, I., Domingo, P. et al 2001. A randomized trial of the discontinuation of primary and secondary prophylaxis against *Pneumocystis carinii* pneumonia after highly active antiretroviral therapy in patients with H1V infection. Grupo de Estudio del SIDA 04(98. N. Eng. J Med. 344:159-167.
10. Kenyon, G. 2001. Resistance study to re-evaluate HAART. Nat. Med. 7:515.
11. Richman, D. D. 2001. HIV chemotherapy. Nature 410:995-1001.
12. Cushion, M. T., Stringer, J. R., and Walzer, P. D. 1991. Cellular and molecular biology of *Pneumocystis carinii*. International Review of Cytology 131:59-107.
13. Stansell, J. D., Osmond, D. H., Charlebois, E., Lavange, L., Wallace, J M, Alexander, B. V.,
Glassroth, J., Kvale, P. A, Rosen, M J. et al 1997. Predictors of *Pneumocystis carinii* pneumonia in HIV-infected persons. Pulmonary Complications of HfV Infection Study Group. American Journal of Respiratory & Critical Care Medicine 155:60-66.
14. Beck, J. M., Warnock, M. L., Curtis, J. L., Sniezek, M. J., Arraj-Peffer, S. M., Kaitreider, H. B., and Shellito, J. E. 1991. Inflammatory Responses to *Pneumocystis Carinii* in Mice Selectively Depleted of Helper T Lymphocytes. Am. J. Respir. Cell Mol. Bioi. 5:186-197.
15. Shellito, J., Suzara, V. V., Blumenfeld, W., Beck, J. M., Steger, H. J., and Ermak, T. H. 1990. A new model of *Pneumocystis carinii* infection in mice selectively depleted of helperT lymphocytes. J. Clin. Invest. 85:1686-1693.
16. Harmsen, A G., and Stankiewicz, M. 1990. Requirement for CD4+ cells in resistance to *Pneumocystis carinii* pneumonia in mice. J. Exp. Med. 172:937-945.
17. Roths, 1 B., and Sidman, C. L. 1992. Both immunity and hyperresponsiveness to *Pneumocystis carinii* result from transfer of CD4+ but not CD8+ T cells into severe combined immunodeficiency mice. J. Clin. Invest 90:673-678.
18. Theus, S. A, Linke, M J., Andrews, R. P., and Walzer, P. D. 1993. Proliferative and cytokine responses to a major surface glycoprotein of *Pneumocystis carinii*. Irifect. Immun. 61:4703-4709.
19. Theus, S. A., Smulian, A. G., Sullivan, D. W., and Walzer, P. D. 1997. Cytokine responses to the native and recombinant forms of the major surface glycoprotein of *Pneumocystis carinii*. Clinical & Experimental Immunology 109:255-260.
20. Murray, H. W., Rubin, B. Y., Masur, H., and Roberts, R. B. 1984. Impaired production of lymphokines and immune (gamma) interferon in the acquired immunodeficiency syndrome. N. Engl. J. Med. 310:883-889.
21. Rudy, T., Opelz, G., Gerlach, R., Danie J, V., and Schimpf, K. 1988. Correlation of in vitro immune defects with impaired gamma interferon response in human-immunodeficiency-virus-infected individuals. Vox Sanguinis 54:92-95.
22. Pesanti, E. L. 1991. Interaction of cytokines and alveolar cells with *Pneumocystis carinii* in vitro. J Inject. Dis. 163:611-616.
23. Chen, W., Havell, E. A., and Harmsen, A. 1992. Importance of endogenous tumor necrosis factor-alpha and gamma interferon in host resistance against *Pneumocystis carinii* infection. Infect. Immun. 60:1279-1284.
24. Garvy, B. A., Ezekowitz, R. A., and Harmsen, A. G. 1997. Role of gamma interferon in the host immune and inflammatory responses to *Pneumocystis carinii* infection. Infect. Immun. 65:373-379.
25. Shear, H. L., Valladares, G., and Narachi, M. A. 1990. Enhanced treatment of *Pneumocystis carinii* pneumonia in rats with interferon-gamma and reduced doses of trimethoprim/sulfamethoxazole. Journal of Acquired Immune Deficiency Syndromes 3:943-948.
26. Beck, J. M., Liggit, H. D., Brunette, E. N., Fuchs, H. J., Shellito, J. E., and Debs, R. J. 1991. Reduction in intensity of *Pneumocystis carinii* pneumonia in mice by aerosol administration of interferon-gamma. Infect. Immun. 59:3859-3862.
27. Debs, R. J., Fuchs, H. J., Philip, R., Montgomery, A. B., Brunette, E. N., Liggitt, D., Patton, J. S., and Shellito, J. E. 1988. Lung-specific delivery of cytokines induces sustained pulmonary and systemic immunomodulation in rats. J Immunol. 140:3482-3488.
28. Burchett, S. K., Weaver, W. M., Westall, J. A., Larsen, A., Kronheim, and Wilson, C. B. 1988. Regulation of tumor necrosis factor cachectin and IL-1 secretion in human mononuclear phagocytes. J. Immunol. 140:3473-3481.
29. Drath, D. B. 1986. Modulation of pUlmonary macrophage superoxide release and tumoricidal activity following activation by biological response modifiers. Immunopharmacology 12:117-126.
30. Sherman, M. P., Loro, M. L., Wong, V. Z., and Tashkin, D. P. 1991. Cytokine- and *Pneumocystis carinii*-induced L-arginine oxidation by murine and human pulmonary alveolar macrophages. Journal of Protozoology 38:234S-2368.
31. Limper, A H., Hoyte, I S., and 8tanding, J. E. 1997. The role of alveolar macrophages in *Pneumocystis carinii* degradation and clearance from the lung. J Clin. Invest. 99:2110-2117.
32. Kolls, I K., Habetz, 8" Shean, M. K., Vazquez, c., BroWll, J. A., Lei, D., Schwarzenberger, P., Ye, P., Nelson, S., Summer, W. R. et al 1999. IFN-gamma and CD8+ T Cells Restore Host Defenses Against *Pneumocystis carinii* in Mice Depleted of CD4+ T Cells. J Immunol 162:2890-2894.
33. Kolls, J. K., Ye, P., and Shellito, J. E. 2001. Gene therapy to modify pulmonary host defenses. Semin. Respir Infect. 16: 18-26.
34. McAllister, F., Steele, C., Zheng, M., Shellito, J, E., and Kolls, J. K. 2005, In Vitro Effector Activity of *Pneumocystis* murina-Specific T-Cytotoxic-I CD8+ T Cells: Role of Granulocyte-Macrophage Colony-Stimulating Factor. Infect Immun 73:7450-7457.
35. Garvy, B. A., WileY, 1 A, Gigliotti, F., and Harmsen, A G. 1997. Protection against *Pneumocystis carinii* pneumonia by antibodies generated from either T helper 1 or T helper 2 responses, Infection & Immunity 65:5052-5056.
36. Lund, F. E., Hollifield, M., Schuer, K, Lines, J. L., Randall, T. D., and Garvy, B. A. 2006. B cells are required for generation of protective effector and memory CD4 cells in response to *Pneumocystis* lung infection. J Immunol. 176:6147-6154.
37. Ledbetter, 1 A., Shu, G., GalJagher, M., and Clark, E. A. 1987. Augmentation of normal and malignant B cell proliferation by monoclonal antibody to the B cell-specific antigen BP50 (CDW40). J Immunol. 138:788-794.
38. Levy, J., Espanol-Boren, T., Thomas, C., Fischer, A., Tovo, P., Bordigoni, P., Resnick, Fasth, A., Baer, M., Gomez, L. et al 1997. Clinical spectrum of X-linked hyper-IgM syndrome. J Pediatr. 131:47-54.
39. Schoenberger, S. P., Toes, R. E., van der Voort, E. I., Offringa, R., and Melief, C. 1. 1998. T-cell help for cytotoxic T lymphocytes is mediated by CD40-CD40L interactions. Nature 393:480-483.
40. Bennett, S. R, Carbone, F. R., Karamalis, F., Flavell, R. A., Miller, J. F., and Heath, W. R 1998. Help for cytotoxic-T-cell responses is mediated by CD40 signalling. Nature 393:478-480.
41. Ridge, J. P., Di Rosa, F., and Matzinger, P. 1998. A conditioned dendritic cell can be a temporal bridge between a CD4+ T-helper and a T-killer cell. Nature 393:474-478.
42. Lane, P., Brocker, T., Hubele, S., Padovan, E., Lanzavecchia, A., and McConnell, F. 1993. Soluble CD40 ligand can replace the normal T cell-derived CD40 ligand signal to B cells in T cell-dependent activation. J Exp. Med 177:1209-1213.
43. Wiley, J. A., and Harmsen, A G. 1995. CD40 ligand is required for resolution of *Pneumocystis carinii* pneumonia in mice. J Immunol. 155:3525-3529.
44. Grewal, r. S., Borrow, P., Pamer, E, G., Oldstone, M. B., and Flavell, R A. 1997. The CD40-CD154 system in anti-infective host defense. Curro Opin. Immunol. 9:491-497.
45. Guo, L., Johnson, R S., and Schuh, J. C. 2000. Biochemical characterization of endogenously formed eosinophilic crystals in the lungs of mice. J Biol Chem, 275:8032-8037.
46. Oz, H. S., Hughes, W. T., Rehg, J. E., and Thomas, E. K. 2000, Effect of CD40 ligand and other immunomodulators on *Pneumocystis carinii* infection in rat model. Microb, Pathog. 29:187-190.
47. Kikuchi, T., Worgall, S., Singh, R., Moore, M. A., and Crystal, R. G. 2000. Dendritic cells genetically modified to express CD40 ligand and pulsed with antigen can initiate antigen-specific humoral immunity independent of CD4+ T cells. Nat. Med. 6:1154-1159.
48. Marcotte, H., Levesque, D., Delanay, K., BourgeauJ. t, A, de Ia, D. R., Brochu, S., and Lavoie, M. C. 1996. *Pneumocystis carinii* infection in transgenic B cell-deficient mice. J Infect. Dis. 173:1034-1037.
49. Theus, S. A, Smulian, A G., Steele, P., Linke, M J., and Walzer, P. D. 1998. Immunization with the major surface glycoprotein of *Pneumocystis carinii* elicits a protective response. Vaccine 16: 1149-1157.
50. Gigliotti, F., Wiley, J. A., and Harmsen, A G. 1998. Immunization with *Pneumocystis carinii* gpA is immunogenic but not protective in a mouse model of *P. carinii* pneumonia. Infect. Immun. 66:3179-3182.
51. Pascale, J. M., Shaw, M. M., Durant, P.]., Amador, A A, Bartlett, M. S., Smith, J. W., Gregory, R. L., and McLaughlin, G. L. 1999. Intranasal immunization confers protection against murine *Pneumocystis carinii* lung infection. Infect. Immun. 67:805-809.
52. Smulian, A G., Sullivan, D. W., and Theus, S. A. 2000. Immunization with recombinant *Pneumocystis carinii* p55 antigen provides partial protection against infection: characterization of epitope recognition associated with immunization. Microbes. Infect. 2:127-136.
53. Zheng, M., Shellito, J. E., Marrero, L., Zhong, Q., Julian, S., Ye, P., Wallace, V., Schwarzenberger, P., and Kolls, J, K. 2001. CD4(+) T cell-independent vaccination against *Pneumocystis carinii* in mice, J Clin. Invest 108:1469-1474.
54. Steele, C., Marrero, L., Swain, S., Harmsen, A G., Zheng, M., Brown, G. D" Gordon, S" Shellito, J. E" and Kolls, J. K. 2003, Alveolar Macrophage-mediated Killing of *Pneumocystis carinii* f. sp. *muris* Involves Molecular Recognition by the Dectin-1 {beta)-Glucan Receptor. J. Exp. Med 198:1677-1688.
55. Numasaki, M., Watanabe, M., Suzuki, T., Takahashi, H., Nakamura, A., McAllister, F., Hishinuma, T., Goto, J., Lotze, M. T., Kolls, J. K. et al 2005. IL-17 Enhances the Net Angiogenic Activity and In Vivo Growth of Human Non-Small Cell Lung Cancer in SC1D Mice through Promoting CXCR-2-Dependent Angiogenesis. J Immunol 175:6177.6189.
56. Lee, L. H., Gigliotti, F., Wright, T. W., Simpson.Haidaris, P J., Weinberg, G. A., and Haidaris, C. G. 2000. Molecular characterization of KEXI, a kexin-like protease in mouse *Pneumocystis carinii*. Gene 242:141-150.
57. Gigliotti, F., Garvy, B. A., Haidaris, C. G., and Harmsen, A. G. 1998. Recognition of *Pneumocystis carinii* antigens by local antibody-secreting cells following resolution of *P. carinii* pneumonia in mice. J Infect. Dis. 178:235-242.
58. Kling, H. M., ShipJey, T. W., Patil, S., Morris, A., and Norris, K. A. 2009. *Pneumocystis* colonization in immunocompetent and simian immunodeficiency virus-infected cynomolgus macaques. J Infect. Dis. 199:89-96.
59. Estcourt, M. J., Ramsay, A J., Brooks, A., Thomson, S. A., Medveckzy, C J., and Ramshaw, L A. 2002. Prime-boost immunization generates a high frequency, high-avidity CD8(+) cytotoxic T lymphocyte population. Int. Immunol. 14:31-37.
60. Cox, K. S., Clair, J. H., Prokop, M. T., Sykes, K J., Dubey, S. A., Shiver, J. W., Robertson, M. N., and Casimiro, D. R. 2008. DNA gagladenovirus type 5 (Ad5) gag and Ad5 gaglAd5 gag vaccines induce distinct T-cell response profiles. J Virol. 82:8161-8171.
61. Hanke, T., Goonetilleke, N., McMichael, A J., and Dorrell, L. 2007. Clinical experience with plasmid DNA- and modified vaccinia virus Ankara-vectored human immunodeficiency virus type 1 clade A vaccine focusing on T-cell induction. J Gen. Virol. 88:1-12.
62. Karkhanis, L. U., and Ross, T M 2007 Mucosal vaccine vectors: replication-competent versus replication-deficient poxviruses. Curr. Pharm. Des. 13:2015-2023.
63. Duerr, R H., Taylor, K. D., Brant, S. R., Rioux, J. D., Silverberg, M. S., Daly, M. J., Steinhart, A H., Abraham, C., Regueiro, M., Griffiths, A et al 2006. A Genome-Wide Association Study Identifies IL23R as an Inflammatory Bowel Disease Gene. Sci 314:1461-1463.
64. Happel, K. I., Lockhart, E. A, Mason, C. M., Porretta, E., Keoshkerian, E., Odden, A R, Nelson, S., and Ramsay, A. J. 2005. Pulmonary interleukin-23 gene delivery increases local T-cell immunity and controls growth of *Mycobacterium tuberculosis* in the lungs. Inject Immun 73:5782-5788.
65. Reay, J., Kim, S. H., Lockhart, E., Kolls, J., and Robbins, P. D. 2009. Adenoviral-mediated, intratumor gene transfer of interleukin 23 induces a therapeutic antitumor response. Cancer Gene Ther.
66. Morelli, A E., Larregina, A. T., Ganster, R. W., Zahorchak, A. F., Plowey, J. M., Takayama, T., Logar, A J., Robbins, P. D., Falo, L. D., and Thomson, A W. 2000. Recombinant adenovirus induces maturation of dendritic cells via an N F-kappaB-dependent pathway. J Virol. 74:9617-9628.
67. Kikuchi, T., Moore, M. A, and Crystal, R G. 2000. Dendritic cells modified to express CD40 ligand elicit therapeutic immunity against preexisting murine tumors. Blood 96:91-99.
68. Zhong, L., Granelli-Pipemo, A., Pope, M., Ignatius, R, Lewis, M. G., Frankel, S. S., and Steinman, R M. 2000. Presentation of SIVgag to monkey T cells using dendritic cells transfected with a recombinant adenovirus. Eur. J Immunol. 30:3281-3290.
69. Neeson, P., Boyer, J., Kumar, S., Le",is, M. G., Mattias, L., Veazey, R., Weiner, D., and Paterson, Y. 2006. A DNA prime-oral *Listeria* boost vaccine in rhesus macaques induces a SIV-specific CD8 T cell mucosal response characterized by high levels of alpha4beta7 integrin and an effector memory phenotype. Virology 354:299-315.
70. Shean, M. K., Baskin, G., Sullivan, D., Schurr, J., Cavender, D. E., Shellito, J. E., Schwarzenberger, P. O., and Kolls, J. K. 2000. Immunomodulation and adenoviral gene transfer to the lungs of nonhuman primates. Hum. Gene Ther. 11:1047-1055.
71. Sullivan, D. E., Dash, S., Du, H., Hiramatsu, N., Aydin, F., Kolls)., Blanchard)., Baskin, G., and Gerber, M. A. 1997. Liver-Directed Gene Transfer in Non-human Primates. Hum. Gene Ther. 8:1195-1206.

Publications by Colleagues:
1. Steele C, Marrero L, Shellito l E, Kolls J K. Alveolar macrophage-mediated killing of *Pneumocystis carinii* f. sp. *muris* involves pattern recognition by the Dectin-1 beta-glucan receptor. J. Exp Med. 2003; 198:1677-1688

2. Happel K I, Zheng M, Quinton L J, Lockhart E, Ramsay A J, Shellito J E, Schurr J R, Bagby G J, Nelson S, Kolls J K. Cutting Edge: Roles of Toll-Like Receptor 4 and IL-23 in IL-17 Expression in Response to *Klebsiella pneumoniae* Infection. J. Immunol 2003; 170:4432-4436.
3. Kolls J K, Kanaly S T, Ramsay A J. Interleukin 17: an emerging role in lung Inflammation. Am J Respir Cell Mol Biol 2003 January; 28(1):9-11
4. McAllister F, Steele C, Zheng M, Young Erana, Shellito 1 E, Marrero L, Kolls J K. Tel CD8+ T-cells are effector cells against *Pneumocystis* in mice. J Immunol 2004; 172: 1132-1138.
5. Kalis J K and Linden A. IL-17 family members and Inflammation. Immunity. 2004Oct; 21(4):467-76.
6. Steele C, Shellito J E, Kolls J K. Immunity against the opportunistic fungal pathogen *Pneumocystis*. Medical Mycology 2004; 43:1-19.
7. Schurr J R, Young E, Byrne P, Steele C, Happel K, Shellito J E, Kolls J K. Central role of TLR4 signaling and host defense in experimental gram negative pneumonia. Infection and Immunity 2005; 73:532-545.
8. Mc Allister F, Henry A, Kreindler J L, Dubin P J, Ulrich L, Steele C, Finder J D, Pilewski J M, Carreno B, Goldman S J, Pirhonen J, and Kolls J K. Role of IL-17A, IL-17F and the IL-17 receptor in regulating Gro-alpha and G-CSF in Bronchial Epithelium: implications for airway inflammation in cystic fibrosis. J Immunol 175(1):404-12, 2005.
9. Happel Kl, Dubin P J, Zheng M, Ghilardi N, Lockhart C, Quinton U, Odden A R, Shellito J E, Bagby G J, Nelson S, Kolls J K Divergent roles of IL-23 and IL-12 in host defense against *Klebsiella pneumoniae* J Exp Med 2005; 202:761-769.
10. Ruan S, Young E, Luce M J, Reiser J, Kolls J K, Shellito J E. Conditional expression of interferon-gamma to enhance host responses to pulmonary bacterial infection. Pulmonary Pharmacology and Therapeutics. 2005; 19:251-257.
11. Zheng M, Ramsay A J, Robichaux M B, Norris K A, Kliment C, Crowe C, Rapaka R R, Steele C, McAllister F, Shellito J E, Marrero L, Schwarzenberger P, Zhong Q, and Kolls J K. CD4+ T cell-independent DNA vaccination against opportunistic infections J. Clin. Invest., 2005; 115: 3536-3544
12. McAllister F, Steele C, Zheng M, Shellito J E, Kolls J K. In vitro effector activity of *Pneumocystis*-specific T cytotoxic-I CD8+ T-cells: role of G M-CSF. Infec Immun 2005; 73:7450-7457.
13. McAllister F, Ruan S, Kolls J K, Shellito J E. CXCR3 and I P-I0 *Pneumocystis* pneumonia. J. Immunology 2006; 177: 1846-1854.
14. McKinley L, Logar A J, McAllister F, Zheng M, Steele C, and Kolls J K. Regulatory T Cells Dampen Pulmonary Inflammation and Lung Injury in an Animal Model of *Pneumocystis* Pneumonia. J. Immunol. 177(9):6215-6226, 2006.
15. Rapaka R R, Goetzman E S, Zheng M, Vockley J, McKinley L, Kolls J K, Steele C. Enhanced defense against *Pneumocystis carinii* mediated by a novel dectin-1 receptor Fc fusion protein. J. Immunol. 178(6):3702-12, 2007.
16. Hsu H C, Yang P, Wang J, Wu Q, Myers R, Chen J, Yi J, Guentert T, Tousson A, Stanus A L, Le T V, Lorenz R G, Xu H, Kolls J K, Carter R H, Chaplin D D, Williams R W, Mountz J D. Interleukin 17-producing T helper cells and interleukin 17 orchestrate autoreactive genninal center development in autoimmune BXD2 mice. Nat Immunol. 2008 February; 9(2): 166-75

17. Aujla S, Chan Y C, Zheng M, Fei M, Askew D J, Pociask D A, Reinhart T A, McAllister F, Edeal J, Gaus K, Husain S, Kreindler J L, Dubin P J, Pilewski 1M, Myerburg M M, Mason C A, 1wakura Y, and Kolls J K. IL-22 mediates mucosal host defense against gram negative bacterial pneumonia. Nat Med. 2008 March; 14(3):275-81.

18. Raffatellu M, Santos R L, Verhoeven D, Wilson R P, Winter S E, Godinez I, Sankaran S, Paixao T, George M D, Gordon M A, Kolls J K, Dandekar S, and Baumler A J. IL-17 orchestrates a mucosal response against *Salmonella* dissemination from the gut. Nat Med. 2008 April; 14(4):421-8.

19. Ruan S, McKinley L, Zheng M, Rudner X, Kolls J K, Shellito J E. Interleukin-12 and host defense against murine *Pneumocystis* pneumonia. Infection and Immunity 2008; 76: 2130-2137.

20. Ouyang W, Kolls J K, Zheng Y. The biological functions of T helper 17 cell effector cytokines in inflammation. Immunity. 2008 April; 28(4):454-67.

21. Kolls J K, McCray P B Jr, Chan Y R. Cytokine-mediated regulation of antimicrobial proteins. Nat Rev Immunol. 2008 November; 8(ll):829-35.

22. Chan Y R, Liu J, Pociask D, Zheng M, Mietzner T A, Berger T, Mak T, Clifton M, Strong R K, Ray P, Kolls J K. Lipocalin 2 is required for pulmonary host defense against *Klebsiella* infection. 1. Immunol. 2009, 182:4493-4494.

MISCELLANEOUS

The complete disclosures of all references and publications cited in this disclosure are hereby incorporated by reference in their entirety, as is the entire disclosure of priority application 61/294,252, filed Jan. 12, 2010. In the event of an otherwise irreconcilable conflict, the present specification shall control.

What is claimed:

1. A vector comprising a polynucleotide encoding a peptide consisting of the amino acid sequence DDDGKTVDGP SSLVLRALIN GVNNGRNGLG SIYVFASGNG GIYEDNCNFD GYANSVFTITIGGIDK HGKRLKYSEA CSSQLAVTYAG GSA (SEQ ID NO: 1).

2. The vector of claim 1, wherein the vector is an adenoviral vector.

3. An isolated cell comprising the vector of claim 1.

4. A method of inducing an immune response in a subject, the method comprising administering to the subject an effective amount of a composition comprising a vector comprising a polynucleotide encoding a peptide consisting of the amino acid sequence DDDGKTVDGP SSLVLRALIN GVNNGRNGLG SIYVFASGNG GIYEDNCNFD GYANSVFTITIGGIDK HGKRLKYSEA CSSQLAVTYAG GSA (SEQ ID NO: 1) and a pharmaceutically acceptable excipient.

5. The method of claim 4, wherein the immune response is sufficient to prevent or treat a disease caused by *Pneumocystis* infection in the subject.

6. The method of claim 4, where in the subject is immunocompromised or has chronic obstructive pulmonary disease.

7. The method of claim 4, wherein the composition is administered by intramuscular, intranasal, or mucosal administration.

8. The method of claim 4, further comprising a subsequent administration of the vector.

9. A vaccine comprising an effective amount of the vector of claim 1 and an adjuvant.

10. A method of preventing or treating a disease caused by *Pneumocystis* infection in a subject, the method comprising administering to the subject the vaccine of claim 9.

11. The method of claim 10, wherein the vaccine is administered by intramuscular, intranasal, or mucosal administration.

12. The method of claim 11, further comprising a subsequent administration of the vaccine.

* * * * *